(12) United States Patent
Asch et al.

(10) Patent No.: US 7,429,636 B2
(45) Date of Patent: *Sep. 30, 2008

(54) ORGANOHYDROGENSILICON COMPOUNDS

(75) Inventors: Karmen Karen Asch, Beaverton, MI (US); Brian Douglas Chapman, Midland, MI (US); Loren Dean Durfee, Midland, MI (US); Robert Michael Hensel, Sanford, MI (US); Timothy Paul Mitchell, Clio, MI (US); James Steven Tonge, Sanford, MI (US); Paul Cornelius Van Dort, Sanford, MI (US)

(73) Assignee: Dow Corning Corporation, Midland, MI (US)

( * ) Notice: Subject to any disclaimer, the term of this patent is extended or adjusted under 35 U.S.C. 154(b) by 383 days.

This patent is subject to a terminal disclaimer.

(21) Appl. No.: 10/512,750

(22) PCT Filed: Apr. 29, 2003

(86) PCT No.: PCT/US03/13203

§ 371 (c)(1),
(2), (4) Date: May 20, 2005

(87) PCT Pub. No.: WO03/093349

PCT Pub. Date: Nov. 13, 2003

(65) Prior Publication Data

US 2005/0256286 A1    Nov. 17, 2005

Related U.S. Application Data

(60) Provisional application No. 60/377,425, filed on May 1, 2002.

(51) Int. Cl.
C08G 77/12 (2006.01)
C08G 77/20 (2006.01)

(52) U.S. Cl. .......................................... 528/31; 528/32
(58) Field of Classification Search .................... 528/31
See application file for complete search history.

(56) References Cited

U.S. PATENT DOCUMENTS

| 2,868,766 A | 1/1959 | Johannson |
| 2,994,684 A | 8/1961 | Johannson |
| 3,002,951 A | 10/1961 | Johannson |
| 3,159,601 A | 12/1964 | Ashby ........................ 260/46.5 |
| 3,159,662 A | 12/1964 | Ashby |
| 3,220,972 A | 11/1965 | Lamoreaux ................ 260/46.5 |
| 3,296,291 A | 1/1967 | Chalk et al. .............. 260/448.2 |
| 3,372,178 A | 3/1968 | Wu |
| 3,410,886 A | 11/1968 | Joy |
| 3,419,593 A | 12/1968 | Willing .................... 260/448.2 |
| 3,516,946 A | 6/1970 | Modic ........................ 252/429 |
| 3,814,730 A | 6/1974 | Karstedt ..................... 260/46.5 |
| 3,928,629 A | 12/1975 | Chandra et al. ............. 427/387 |
| 3,989,668 A | 11/1976 | Lee et al. ................... 260/46.5 |
| 3,996,195 A | 12/1976 | Sato et al. |
| 4,245,079 A | 1/1981 | Matsumoto et al. |
| 4,427,801 A * | 1/1984 | Sweet ........................ 523/212 |
| 4,461,867 A | 7/1984 | Surprenant .................. 524/788 |
| 4,525,400 A | 6/1985 | Surprenant .................... 428/54 |
| 4,525,566 A | 6/1985 | Homan et al. ................. 528/17 |
| 4,616,076 A | 10/1986 | Ona et al. ..................... 528/15 |
| 4,681,963 A | 7/1987 | Lewis ......................... 556/453 |
| 4,705,765 A | 11/1987 | Lewis ......................... 502/152 |
| 4,726,964 A | 2/1988 | Isobe et al. ................ 427/54.1 |
| 4,849,491 A | 7/1989 | Ogawa et al. ................. 528/15 |
| 4,900,779 A | 2/1990 | Leibfried |
| 4,902,731 A * | 2/1990 | Leibfried ..................... 523/222 |
| 5,036,117 A | 7/1991 | Chung et al. ................. 522/172 |
| 5,097,054 A | 3/1992 | Yamamoto et al. .......... 556/451 |
| 5,162,445 A | 11/1992 | Powers et al. |
| 5,175,325 A | 12/1992 | Brown et al. .................... 556/9 |
| 5,200,543 A * | 4/1993 | Inomata et al. .............. 556/434 |
| 5,290,841 A * | 3/1994 | Enami et al. ................. 524/265 |
| 5,344,906 A | 9/1994 | Westall |
| 5,378,790 A | 1/1995 | Michalczyk et al. .......... 528/35 |
| 5,412,055 A | 5/1995 | Loo ............................. 528/15 |
| 5,426,167 A | 6/1995 | Powers et al. |
| 5,436,308 A | 7/1995 | Durfee et al. |
| 5,525,696 A | 6/1996 | Herzig et al. ................. 528/15 |
| 5,536,803 A * | 7/1996 | Fujiki et al. .................... 528/15 |
| 5,545,831 A | 8/1996 | Kaiya et al. ................. 524/731 |
| 5,545,837 A | 8/1996 | Kobayashi ................... 556/460 |
| 5,548,051 A | 8/1996 | Michalczyk et al. .......... 528/15 |
| 5,575,831 A | 11/1996 | Yamamura et al. ............ 75/614 |

(Continued)

FOREIGN PATENT DOCUMENTS

EP        0 464 706        1/1992

(Continued)

OTHER PUBLICATIONS

Kurian et al., Novel Cyclosiloxane-Based Networks, Polymer Preprints 2003, 44(1)m 33-34.

(Continued)

*Primary Examiner*—Randy Gulakowski
*Assistant Examiner*—Robert Loewe
(74) *Attorney, Agent, or Firm*—Patricia M. Scaduto

(57) ABSTRACT

Organohydrogensilicon compounds containing at least one silicon-bonded hydrogen atom per molecule and at least one cyclosiloxane.

25 Claims, No Drawings

U.S. PATENT DOCUMENTS

| | | | |
|---|---|---|---|
| 5,581,008 A | 12/1996 | Kobayashi | 556/434 |
| 5,656,711 A * | 8/1997 | Fukuda et al. | 528/15 |
| 5,670,596 A | 9/1997 | Razzano et al. | |
| 5,691,435 A | 11/1997 | Herzig et al. | 528/15 |
| 5,830,969 A | 11/1998 | Ahmed Jallouli et al. | |
| 5,883,215 A | 3/1999 | Bischoff et al. | |
| 5,985,462 A | 11/1999 | Herzig et al. | 428/447 |
| 6,093,782 A | 7/2000 | Herzig et al. | 528/15 |
| 6,127,502 A * | 10/2000 | Krahnke et al. | 528/10 |
| 6,160,150 A | 12/2000 | Krahnke et al. | 556/451 |
| 6,177,519 B1 | 1/2001 | Chung et al. | |
| 6,184,407 B1 * | 2/2001 | Yoshitake et al. | 556/434 |
| 6,235,832 B1 | 5/2001 | Deng et al. | 524/525 |
| 6,252,100 B1 | 6/2001 | Herzig | 556/450 |
| 6,300,452 B1 | 10/2001 | Jukarainen et al. | 528/15 |
| 6,303,729 B1 | 10/2001 | Sato | 528/25 |
| 6,313,255 B1 | 11/2001 | Rubinsztajn | 528/27 |
| 6,353,075 B1 | 3/2002 | Hupfield et al. | |
| 6,528,584 B2 | 3/2003 | Kennedy et al. | 525/101 |
| 6,605,734 B2 | 8/2003 | Roy et al. | 556/9 |
| 6,797,772 B2 | 9/2004 | Nakayoshi et al. | |
| 2003/0022991 A1 | 1/2003 | Kennedy et al. | 525/100 |

FOREIGN PATENT DOCUMENTS

| | | |
|---|---|---|
| EP | 0259711 | 3/1994 |
| EP | 0 416 471 | 1/1999 |
| EP | 0 979 837 | 2/2000 |
| EP | 0600512 | 2/2000 |

OTHER PUBLICATIONS

Kurian et al., Novel Tricomponent Membranes Containing Poly(Ethylene Glycol)/Poly(Pentamethylcyclopentasiloxane)/pOly(Dimethylsiloxane)Domains, Journal of Polymer Science: Part A: Polymer Chemistry, vol. 40, 3093-3102 (2002).

Kurian et al., Synthesis and Characterization of Novel Amphiphilic Block Copolymers Di-Tri-, Multi-, and Star Blocks of Peg and Pib, Journal of Polymer Science: Part A: Polymer Chemistry, vol. 38, 3200-3209 (2000).

Kurian et al., Novel Tricontinuous Hydrophilic-Lipophilic-Oxyphilic Membranes: Synthesis and Characterization*, Journal of Polymer Science: Part A: Polymer Chemistry, vol. 40, 1209-1217 (2002).

Backer M et al: "29Si chemical shift tensors of silyl silicate cages." Solid State Nuclear Magnetic Resonance. Netherlands Dec. 1997, vol. 9, No. 2-4, Dec. 1997, pp. 241-255, XP002248265 ISSN: 0926-2040 table 1.

Koyava Na A et al: "Synthesis of organocyclosiloxanes with a pre-determined arrangement of functional groups on the silicon atoms" Journal of General Chemistry of the USSR, vol. 50, No. 8, 1980, pp. 1461-1465, XP009014152 ISSN: 0022-1279 the whole document.

Sokolow N N et al: "Organocyclosiloxanes. I. Methylchlorocyclsosiloxanes" Journal of General Chemistry of the USSR, vol. 26, 1956, pp. 1061-1063, XP009014155 USSN: 0022-1279 the whole document.

Sokolow N N et al: "Organocyclosiloxanes. II. Ethylchlorocyclosiloxanes" Journal of General Chemistry of the USSR, vol. 26, 1956, pp. 2545-2547, XP009014153 ISSN: 0022-1279 the whole document.

Sakiyama M et al: "The selective halogenation of methylhydropolysiloxanes: syntheses of methylhalopolysiloxanes and their derivatives" Bulletin of the Chemical Society of Japan, vol. 38, No. 12, 1965, pp. 2182-2186, XP009014156 ISSN: 0009-2673 the whole document.

Andrianov N A et al: "Substitution reactions in organocyclosiloxanes containing functional groups attached to the silicon atom" Chemistry of Heterocyclic Compounds, vol. 8, 1972, pp. 1068-1070, XP009014147 ISSN: 0009-3122 the whole document.

Andrianov K A et al: "Heterofunctional condensation of chlorosilanes with tetra- and hexaphenylsiloxanediols" Chemistry of Heterocyclic Compounds, vol. 8, 1972, pp. 810-812, XP009014148 ISSN: 0009-3122 the whole document.

* cited by examiner

ORGANOHYDROGENSILICON COMPOUNDS

CROSS REFERENCES TO RELATED APPLICATIONS

The present application is a US national stage filing under 35 USC 371 and claims priority from PCT application No. PCT/USS03/13203 filed on Apr. 29, 2003 and U.S. application No. 60/377,425 filed on May 1, 2002. The above applications are incorporated by reference in their entirety.

The invention relates to organohydrogensilicon compounds containing at least one silicon-bonded hydrogen atom per molecule and at least one cyclosiloxane.

Hydrosilylation is a well known method for coupling different materials. Generally for hydrosilylation one needs a material having at least one aliphatic unsaturation and a material having at least one SiH group. Depending on the average number of SiH to aliphatic unsaturation present in the molecules, this coupling may include chain extension or crosslinking/curing. Silicone compositions which cure by hydrosilylation are useful in a wide variety of applications to produce coatings, elastomers, adhesives, foams or fluids. The basic constituents of silicone compositions which cure by hydrosilylation include an alkenylated polydiorganosiloxane, typically a linear polymer with terminal alkenyl groups, a polyorganohydrogensiloxane crosslinking agent, designed to cross-link the alkenylated polydiorganosiloxane and a catalyst, to catalyze the aforementioned cross-linking reaction.

Improvements in the performance of compositions which cure by hydrosilylation are continuously being sought with respect to, for example, ease of cure, i.e. the decrease in cure times at relatively low temperatures, extended working time of a formulated bath, i.e. longer thin film and bulk bath life, anchorage of coatings to a substrate release performance and particularly for high catalyst coatings such as release coatings, maintenance of exceptional performance in the aforementioned areas with decreased catalyst level and therefore decreased cost.

A critical parameter in achieving the optimal performance for compositions which cure by hydrosilylation is the structure of the polyorganohydrogensiloxane cross-linking agent. Standard structures which are commonly used include trimethylsilyl endcapped methylhydrogensiloxane polymers, trimethylsilyl endcapped methylhydrogen, dimethyl siloxane copolymers and hydrogendimethylsilyl endcapped dimethylsiloxane polymers. Variations to include branching or resinous structures are also known.

The instant invention teaches novel organohydrogensilicon compounds containing at least one silicon-bonded hydrogen atom per molecule and at least one cyclosiloxane which are useful in hydrosilylation reactions.

The present invention relates to organohydrogensilicon compounds containing at least one silicon-bonded hydrogen atom per molecule and at least one cyclosiloxane.

The present invention relates to organohydrogensilicon compounds containing at least one silicon-bonded hydrogen atom per molecule described by formula (I)

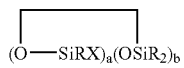

where each R is independently selected from a hydrogen atom and a monovalent hydrocarbon group comprising 1 to 20 carbon atoms which is free from aliphatic unsaturation, a is an integer from 1 to 18, b is an integer from 1 to 19, a+b is an integer from 3 to 20, each X is an independently selected functional group selected from a halogen atom, an ether group, an alkoxy group, an alkoxyether group, an acyl group, an epoxy group, an amino group, or a silyl group, or a -Z-$R^4$ group, where each Z is independently selected from an oxygen and a divalent hydrocarbon group comprising 2 to 20 carbon atoms, each $R^4$ group is independently selected from —$BR_uY_{2-u}$, —$SiR_vY_{3-v}$, or a group described by formula (II):

$$(Y_{3-n}R_nSiO_{1/2})_c(Y_{2-o}R_oSiO_{2/2})_d(Y_{1-p}R_pSiO_{3/2})_e(SiO_{4/2})_f(CR_qY_{1-q})_g(CR_rY_{2-r})_h(O(CR_sY_{2-s})_i(CR_tY_{3-t})_j$$

where B refers to boron, each R is as described above, the sum of c+d+e+f+g+h+i+j is at least 2, n is an integer from 0 to 3, o is an integer from 0 to 2, p is an integer from 0 to 1, q is an integer from 0 to 1, r is an integer from 0 to 2, s is an integer from 0 to 2, t is an integer from 0 to 3, u is an integer from 0 to 2, v is an integer from 0 to 3, each Y is an independently selected functional group selected from a halogen atom, an ether group, an alkoxy group, an alkoxyether group, an acyl group, an epoxy group, an amino group, or a silyl group, or a Z-G group, where Z is as described above, each G is a cyclosiloxane described by formula (III):

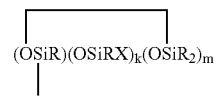

where R and X are as described above, k is an integer from 0 to 18, m is an integer from 0 to 18, k+m is an integer from 2 to 20, provided in formula (II) that one of the Y groups is replaced by the Z group bonding the $R^4$ group to the cyclosiloxane of formula (I), and provided further (a) at least one X group of Formula (I) is a -Z-$R^4$ group, (b) if Z is a divalent hydrocarbon group, a=1, c=2, e+f+g+h+i+j=0 and d>0, then at least one d unit (ie. $Y_{2-o}R_oSiO_{2/2}$) contain a -Z-G group or the c units (ie. $Y_{3-n}R_nSiO_{1/2}$) have no -Z-G group or at least two -Z-G groups, (c) if Z is a divalent hydrocarbon group, a=1, c=2 and d+e+f+g+b+i+j=0, then the c units (ie. $Y_{3-n}R_nSiO_{1/2}$) have no -Z-G group or at least two -Z-G groups, and (d) if g+h+i+j>0 then c+d+e+f>0.

The present invention also relates to organohydrogensilicon compounds containing at least one silicon-bonded hydrogen atom per molecule described by formula (I)

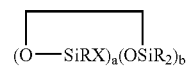

where each R is independently selected from a hydrogen atom and a monovalent hydrocarbon group comprising 1 to 20 carbon atoms which is free from aliphatic unsaturation, a is an integer from 1 to 18, b is an integer from 2 to 19, a+b is an integer from 3 to 20, each X is an independently selected functional group selected from a halogen atom, an ether group, an alkoxy group, an alkoxyether group, an acyl group, an epoxy group, an amino group, or a silyl group, or a -Z-$R^4$ group, where each Z is independently selected from an oxygen and a divalent hydrocarbon group comprising 2 to 20 carbon atoms, each $R^4$ group is independently selected from $-BR_uY_{2-u}$, $-SiR_vY_{3-v}$, or a group described by formula (II):

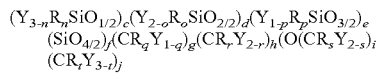

where B refers to boron, each R is as described above, the sum of c+d+e+f+g+h+i+j is at least 2, n is an integer from 0 to 3, o is an integer from 0 to 2, p is an integer from 0 to 1, q is an integer from 0 to 1, r is an integer from 0 to 2, s is an integer from 0 to 2, t is an integer from 0 to 3, u is an integer from 0 to 2, v is an integer from 0 to 3, each Y is an independently selected functional group selected from a halogen atom, an ether group, an alkoxy group, an alkoxyether group, an acyl group, an epoxy group, an amino group, or a silyl group, or a Z-G group, where Z is as described above, each G is a cyclosiloxane described by formula (III):

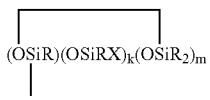

where R and X are as described above, k is an integer from 0 to 18, m is an integer from 0 to 18, k+m is an integer from 2 to 20, provided in formula (II) that one of the Y groups is replaced by the Z group bonding the $R^4$ group to the cyclosiloxane of formula (I), and provided further (a) at least one X group of Formula (I) is a -Z-$R^4$ group, (b) if Z is a divalent hydrocarbon group, a=1, c=2, e+f+g+h+i+j=0 and d>0, then at least one d unit (ie. $Y_{2-o}R_oSiO_{2/2}$) contain a -Z-G group or the c units (ie. $Y_{3-n}R_nSiO_{1/2}$) have no -Z-G group or at least two -Z-G groups, (c) if Z is a divalent hydrocarbon group, a=1, c=2 and d+e+f+g+h+i+j=0, then the c units (ie. $Y_{3-n}R_n$-$SiO_{1/2}$) have no -Z-G group or at least two -Z-G groups, and (d) if g+h+i+j>0 then c+d+e+f>0.

As used herein, the term "aliphatic unsaturation" refers to a carbon-carbon multiple bond.

In formulas (I), (II), and (III), each R group is independently selected from a hydrogen atom and a monovalent hydrocarbon group comprising 1 to 20 carbon atoms free from aliphatic unsaturation. Each monovalent hydrocarbon group of R can be linear, branched or cyclic. Each monovalent hydrocarbon group of R can be unsubstituted or substituted with halogen atoms. The monovalent hydrocarbon group of R can be exemplified by alkyl groups such as methyl, ethyl, propyl, butyl, hexyl, octyl, 3,3,3-trifluoropropyl, nonafluorobutylethyl, chloromethyl, and decyl, cycloaliphatic groups such as cyclohexyl, aryl groups such as phenyl, tolyl, and xylyl, chorophenyl, and aralkyl groups such as benzyl, styryl and alpha-methylstyryl. It is preferred that each R group is independently selected from hydrogen atoms, alkyl groups comprising 1 to 8 carbon atoms, or aryl groups comprising 6 to 9 carbon atoms. It is most preferrred that each R group is independently selected from hydrogen, methyl, alpha-methylstyryl, 3,3,3-trifluoropropyl and nonafluorobutylethyl. Each R can be identical or different, as desired.

In formulas (I) and (III), each X is an independently selected functional group selected from a halogen atom, an ether group, an alkoxy group, an alkoxyether group, an acyl group, an epoxy group, an amino group, or a silyl group, or a -Z-$R^4$ group.

The functional groups represented by X are selected from halogen atoms, ether groups, alkoxy groups, alkoxyether groups, acyl groups, groups, epoxy groups, amino groups, or silyl groups. Examples of useful functional groups include chloro, fluoro, bromo, methoxy, ethoxy, isopropoxy, and oxybutylvinyl ether. Other useful functional groups are derived by hydrosilylation of the alkenyl group from methylvinylether, methylvinylketone, vinylacetate, vinylbenzoate, vinylacrylate, vinylstearate, vinyldecanoate, vinylmethacrylate, vinylcyclohexylepoxide, allylglycidylether, vinylcyclohexylepoxidetrimethoxysilane, trimethylvinylsilane, triethylvinylsilane, vinyltrimethoxysilane, vinyltriacetoxysilane, vinylpyridine, phenylvinylether, phenylvinylketone, and allyl aldehyde with an SiH from the siloxane precursor to formulas (I) or (III), where the term siloxane precursor includes the siloxane material used to make the initial formula (I) or (III) material and any initial formula (I) material which can then be further reacted.

When X is a functional group, it is preferred that each X is independently selected from chloro, methoxy, isopropoxy, and groups derived by hydrosilylation of the alkenyl group from hydroxybutylvinyl ether, vinylcyclohexylepoxide, and allylglycidylether with an SiH from the siloxane precursor to formulas (I) or (III), where the term siloxane precursor includes the siloxane material used to make the initial formula (I) or (III) material and any initial formula (I) material which can then be further reacted.

Each X of formulas (I) and (III) may also comprise a Z-$R^4$ group. It is preferred that X is a Z-$R^4$ group. It is more preferred that X includes both -Z-$R^4$ groups and functional groups derived by hydrosilylation of allylglycidyl ether (ie. propylglycidyl ether) or vinylcyclohexylepoxide.

Each Z is independently selected from oxygen and divalent hydrocarbon groups comprising 2 to 20 carbon atoms. Examples of the divalent hydrocarbon group comprising 2 to 20 carbon atoms represented by Z include alkylene radicals such as methylene, ethylene, methylmethylene, propylene, isopropylene, butylene, pentylene, hexylene, and octadecylene; alkenylene radicals such as vinylene, allylene, butenylene, and hexenylene, arylene radicals such as phenylene and xylylene; aralkylene radicals as benzylene; and alkarylene radicals such as tolylene. Preferably, Z is a divalent hydrocarbon group comprising 2 to 18 carbon atoms. It is more preferred for Z to be an alkylene group, with an alkylene group comprising 2 to 8 carbon atoms being most preferred.

Each $R^4$ group is selected from $-BR_uY_{2-u}$, $-SiR_vY_{3-v}$, or a group described by formula (II) $(Y_{3-n}R_nSiO_{1/2})_c(Y_{2-o}R_o$-$SiO_{2/2})_d(Y_{1-p}R_pSiO_{3/2})_e(SiO_{4/2})_f(CR_qY_{1-q})_g(CR_rY_{2-r})_h(O$-$(CR_sY_{2-s})_i(CR_tY_{3-t})_j$, where R, Y, c, d, e, f, g, h, i, j, n, o, p, q, r, s, t, u, v are as described above, provided in formula (II) that one of the Y groups is replaced by the Z group bonding the $R^4$ group to the cyclosiloxane of formula (I).

In formula (I), a is an integer from 1 to 18, b is an integer from 1 to 19, preferably from 2 to 19, and a+b is an integer from 3 to 20.

In formula (II), the sum of c+d+e+f+g+h+i+j is at least 2, preferably from 2 to 5300, more preferably from 2 to 1000. Preferably, subscript c is an integer from 0 to 50, with 2 to 15 being more preferred, and 2 to 10 being most preferred. Preferably, subscript d is an integer from 0 to 5000, with 0 to 1000 being more preferred, and 1 to 50 being most preferred. Preferably, subscript e is an integer from 0 to 48, with 0 to 13 being more preferred, and 0 to 8 being most preferred. Preferably, subscript f is an integer from 0 to 24, with 0 to 6 being more preferred, and 0 to 4 being most preferred. Preferably, subscript g is an integer from 0 to 50, with 0 to 20 being more preferred, and 0 to 10 being most preferred. Preferably, subscript h is an integer from 0 to 50, with 0 to 20 being more preferred, and 0 to 10 being most preferred. Preferably, subscript i is an integer from 0 to 50, with 0 to 20 being more preferred, and 0 to 10 being most preferred. Preferably, subscript j is an integer from 0 to 50, with 0 to 15 being more preferred, and 0 to 10 being most preferred.

In formula (II), n is an integer from 0 to 3, preferably from 2 to 3; o is an integer from 0 to 2, preferably from 1 to 2; p is an integer from 0 to 1, preferably 1; q is an integer from 0 to 1, preferably 1; r is an integer from 0 to 2, preferably from 1 to 2; s is an integer from 0 to 2, preferably from 1 to 2; and t is an integer from 0 to 3, preferably from 2 to 3. Notwithstanding the above, since the $R^4$ group as described by formula (II) is connected to the cyclosiloxane described by formula (I) via a Z group, one of the Y groups present in the $R^4$ group described by formula (II) will be replaced by a Z group.

In addition to a group described by formula (II) each $R^4$ group is independently selected from $-BR_uY_{2-u}$, and $-SiR_vY_{3-v}$ where B refers to boron, u is an integer from 0 to 2, preferably from 1 to 2 and v is an integer from 0 to 3, preferably from 2 to 3. Examples of these $R^4$ groups are derived from borane or silanes, such as for example, trivinylborane, diallyldimethylsilane, divinyldimethylsilane and vinyltrimethylsilane.

Each Y of $R^4$ is an independently selected functional group selected from a halogen atom, an ether group, an alkoxy group, an alkoxyether group, an acyl group, an epoxy group, an amino group, or a silyl group, or a -Z-G group. The functional groups are exemplified as described above for X. The Z group is also as described above.

Each G is a cyclosiloxane described by formula (III):

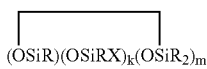

where R and X are as described above, k is an integer from 0 to 18, m is an integer from 0 to 18, and k+m is an integer from 2 to 20.

In formula (III), each k is an integer from 0 to 18, preferably from 1 to 3.

In formula (III), each m is an integer from 0 to 18, preferably from 1 to 10, most preferably from 2 to 4.

The sum of k+m is an integer from 2 to 20, preferably from 2 to 6, most preferably from 2 to 5.

The Y group of formula (II) is preferably a -Z-G group. Although it is not required for there to be any -Z-G groups in the organohydrogensilicon compound of the present invention, it is preferred that on average the organohydrogensilicon compound contain at least 1 -Z-G group with at least 2 -Z-G groups being more preferred.

The $R^4$ group described by formula (II) can be linear, cyclic, branched or resinous. The $R^4$ group described by formula (II) can be a siloxane material where the polymer chain units contain only siloxane units, or it can be a mixture of siloxane units with hydrocarbon units, or oxyhydrocarbon units, where oxyhydrocarbon refers to a hydrocarbon group which also includes at least one oxygen atom. It is preferred that the $R^4$ group is a siloxane material, and more preferred that $R^4$ is a linear siloxane material.

Examples of preferred $R^4$ groups described by formula (II) useful in the invention include $-R_2SiO(R_2SiO)_dSiR_2-Z-G$, $-R_2SiOSiR_3$, $-R_2SiOSiR_2-Y$, $-RSi(OSiR_3)_2$, where d is an integer from 1 to 50 and Z, G, and R are as described above. More preferred $R^4$ groups are as described above when R is methyl, and d is an average of 8.

With respect to the organohydrogensilicon compounds of the present invention it is preferred that (a) at least one X group of Formula (I) is a -Z-$R^4$ group (b) if Z is a divalent hydrocarbon group, a=1, c=2, e+f+g+h+i+j=0 and d>0, then at least one d unit (ie. $Y_{2-o}R_oSiO_{2/2}$) contain a -Z-G group or the c units (ie. $Y_{3-n}R_nSiO_{1/2}$) have no -Z-G group or at least two -Z-G groups, (c) if Z is a divalent hydrocarbon group, a=1, c=2 and d+e+f+g+h+i+j=0, then the c units (ie. $Y_{3-n}R_n$-$SiO_{1/2}$) have no -Z-G group or at least two -Z-G groups, and (d) if g+h+i+j>0 then c+d+e+f>0.

It is also preferred that the organohydrogensilicon compounds of the present invention have a viscosity from 5 to 50,000 mPa·s, more preferred from 10 to 10,000 mPa·s and most preferred from 25 to 2,000 mPa·s.

The organohydrogensilicon compounds of the present invention contain at least one silicon-bonded hydrogen atom per molecule. Preferably, the organohydrogensilicon compounds contain at least 2 silicon-bonded hydrogen atoms per molecule. It is most preferred that the organohydrogensilicon compounds contain at least 3 silicon-bonded hydrogen atoms per molecule.

Examples of the types of organohydrogensilicon compounds included in the scope of the present invention are as follows where Me is methyl, d (which equals $d_1+d_2$) is as described above, and x can range from 1 to 100; preferably 1 to 20.

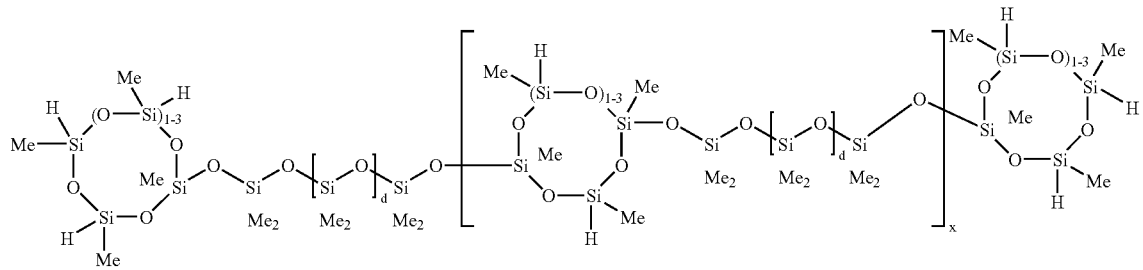

-continued
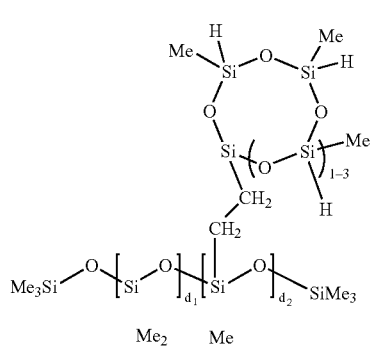
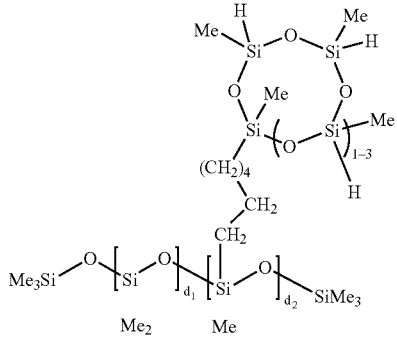
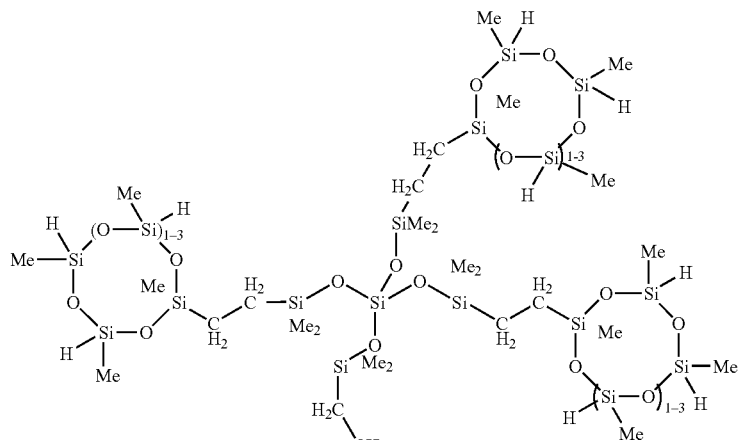
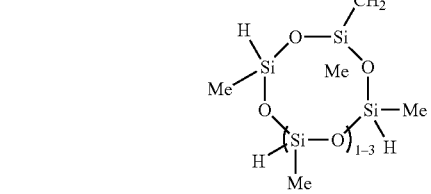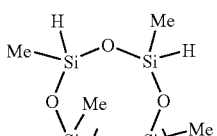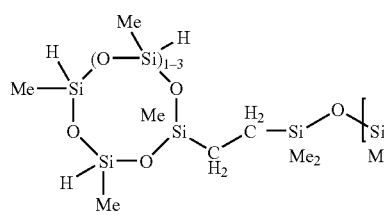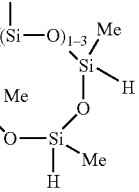
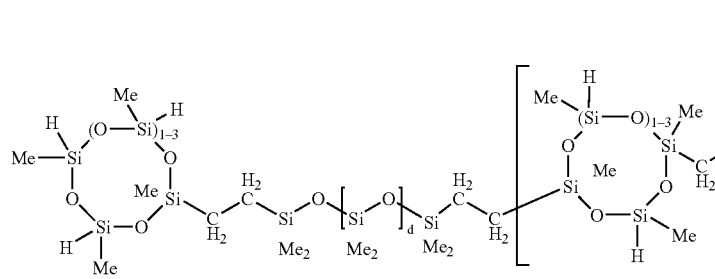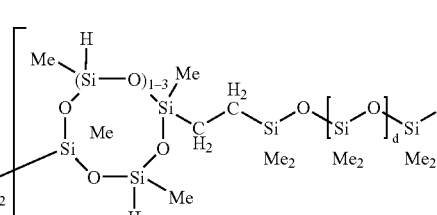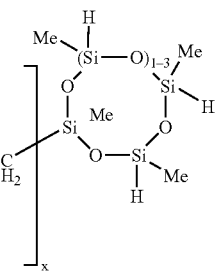

-continued
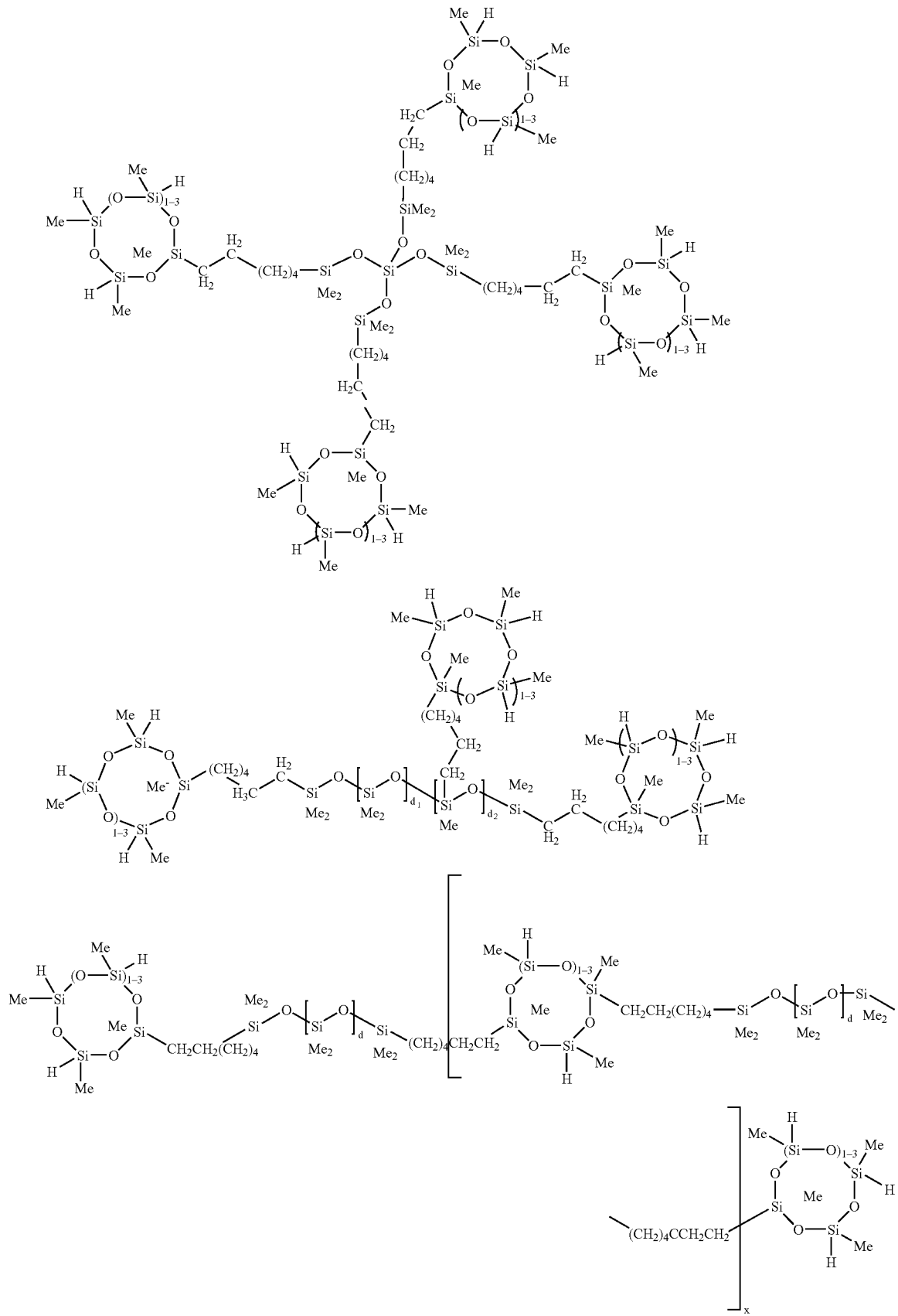

-continued

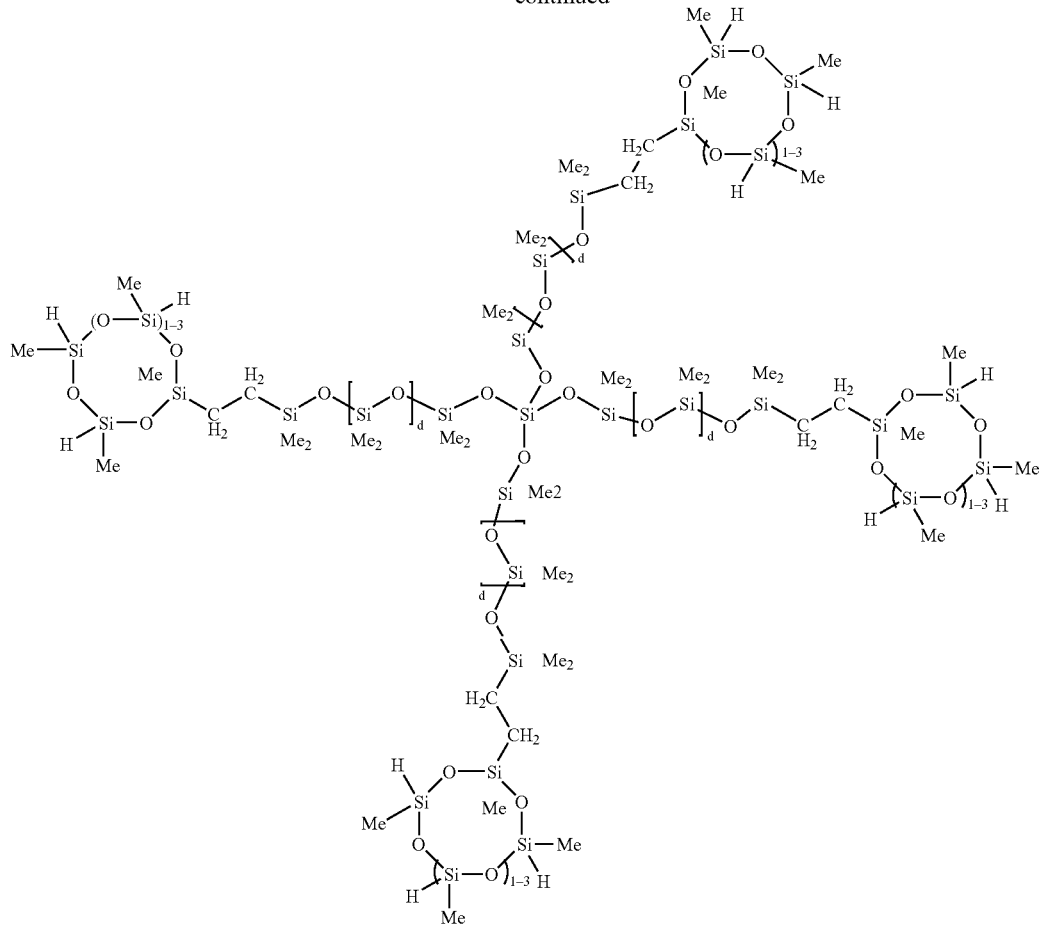

Other examples include the compounds described above where certain of the SiH bonds are replaced by hydrocarbon, oxyhydrocarbon or functional groups. When these SiH bonds are replaced with the above-described groups, it is preferred that 5 to 70% of the SiH bonds are replaced with such other groups, more preferably 5 to 50%, most preferably 10 to 30%

Examples of the hydrocarbon, oxyhydrocarbon and functional groups described above include the types of groups described later in this specification for group A. Preferred groups include functional groups derived by hydrosilylation of allylglycidyl ether (ie. propylglycidyl ether) or vinylcyclo-hexylepoxide, alkyl groups such as 1-hexyl, 1-octyl, and ethylcyclohexene and alkenyl groups such as 5-hexenyl. It is most preferred that the SiH bonds are replaced by functional groups derived by hydrosilylation of allylglycidyl ether.

The most preferred organohydrogensilicon compounds described by formula (I) include the compound described below where Me is methyl, d is an average of 8 and x is an integer from 1 to 15 and the compound described below when 10 to 30% of the SiH bonds are replaced by functional groups derived by hydrosilylation of allylglycidyl ether.

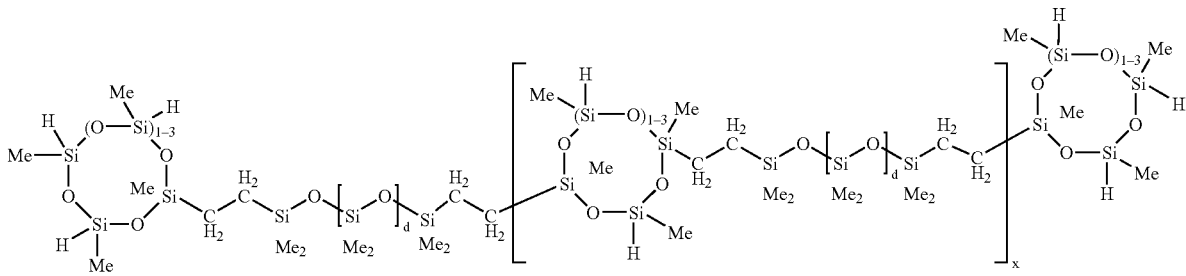

The compounds described by Formula I can be made in a straightforward manner, for example via a platinum catalyzed coupling of methylhydrogen cyclosiloxanes with a reactant containing aliphatic unsaturation, hydroxy functionalities or a mixture of both. The desired product is a function not only of the reactants but also of the reaction stoichiometry. The reaction can be conducted by premixing the reactants followed by catalysis or by using one of the reactants as a controlling reagent. Once an initial organohydrogensilicon compound is prepared, subsequent hydrosilylations or condensations may also be done to replace or convert some of the remaining SiH bonds to other types of groups. After the desired organohydrogensilicon compound is made it is preferred to deactivate the catalyst using an inhibitor.

Generally, the ratio of SiH to aliphatic unsaturation or SiH to hydroxy functionality useful to prepare the organohydrogensilicon compounds of the present invention is at least 2.5:1. It is preferred that a ratio of SiH to aliphatic unsaturation ratio or SiH to hydroxy functionality of 20:1 to 2.5:1 be used with a ratio of 4:1 to 3:1 being most preferred. Notwithstanding the above, if organohydrogensilicon compounds described by formula (I) which are prepared using the above ratios are then further hydrosilylated or condensed, for example to convert or replace some of the remaining SiH groups and form other organohydrogensilicon compounds described by formula (I), the ratio of SiH to aliphatic unsaturation or SiH to hydroxy functionality to be used for these subsequent reactions need not follow the above recommendations but rather is limited only by the amount of SiH which is desired on such final organohydrogensilicon compound.

In one preferred embodiment, the organohydrogensilicon compounds having at least one silicon-bonded hydrogen are prepared by (1) mixing (A) at least one organohydrogen cyclosiloxane comprising at least 2 SiH bonds per molecule and having the formula

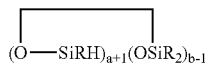

with (B) at least one compound comprising at least one aliphatic unsaturation or at least one hydroxy group per molecule described by $BR_uA_{3-u}$, $SiR_vA_{4-v}$, or a group described by formula $(A_{3-n}R_nSiO_{1/2})_c(A_{2-o}R_oSiO_{2/2})_d(A_{1-p}R_pSiO_{3/2})_e(SiO_{4/2})_f(CR_qA_{1-q})_g(CR_rA_{2-r})_h(O(CR_sA_{2-s})_i(CR_tA_{3-t})_j$ so that ratio of SiH bonds in component (A) to the aliphatic unsaturation or hydroxy group of component (B) is at least 2.5:1; (2) effecting a reaction between components (A) and (B) in the presence of (C) a catalyst to form a reaction mixture comprising organohydrogensilicon compounds having at least one SiH bond per molecule described by formula (I) above; (3) optionally, adding an inhibitor to the reaction mixture; and (4) optionally, isolating the organohydrogensilicon compounds; where B is boron, X, R, a, b, c, d, e, f, g, h, i, j, n, o, p, q, r, s, t, u, v are as defined above, and each A is independently selected from a hydroxy group, a monovalent hydrocarbon group comprising 2 to about 20 carbon atoms having at least one aliphatic unsaturation, a monovalent oxyhydrocarbon group comprising 2 to about 20 carbon atoms having at least one aliphatic unsaturation, or a functional group selected from a halogen atom, an ether group, an alkoxy group, an alkoxyether group, an acyl group, an epoxy group, an amino group, or a silyl group, provided at least one A group has an aliphatic unsaturation or a hydroxy group.

In another preferred embodiment, the organohydrogensilicon compounds having at least one silicon-bonded hydrogen are prepared by (1') mixing (A) at least one organohydrogen cyclosiloxane comprising at least 2 SiH bonds per molecule and having the formula

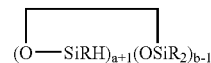

with (C) a catalyst to form a SiH premix; (2') effecting a reaction by adding to the SiH premix (B) at least one compound comprising at least one aliphatic unsaturation or at least one hydroxy group per molecule described by $BR_uA_{3-u}$, $SiR_vA_{4-v}$, or a group described by formula $(A_{3-n}R_nSiO_{1/2})_c(A_{2-o}R_oSiO_{2/2})_d(A_{1-p}R_pSiO_{3/2})_e(SiO_{4/2})_f(CR_qA_{1-q})_g(CR_rA_{2-r})_h(O(CR_sA_{2-s})_i(CR_tA_{3-t})_j$ so that ratio of SiH bonds in component (A) to the aliphatic unsaturation or hydroxy group of component (B) is at least 2.5 to form a reaction mixture comprising organohydrogensilicon compounds having at least one SiH bond per molecule described by formula (I) above; (3') optionally, adding an inhibitor to the reaction mixture; and (4') optionally, isolating the organohydrogensilicon compounds; where B is boron, and A, X, R, a, b, c, d, e, f, g, h, i, j, n, o, p, q, r, s, t, u, and v are as defined above.

In another preferred embodiment, the organohydrogensilicon compounds having at least one silicon-bonded hydrogen are prepared by (1") mixing (B) at least one compound comprising at least one aliphatic unsaturation or at least one hydroxy group per molecule described by $BR_uA_{3-u}$, $SiR_vA_{4-v}$, or a group described by formula $(A_{3-n}R_nSiO_{1/2})_c(A_{2-o}R_oSiO_{2/2})_d(A_{1-p}R_pSiO_{3/2})_e(SiO_{4/2})_f(CR_qA_{1-q})_g(CR_rA_{2-r})_h(O(CR_sA_{2-s})_i(CR_tA_{3-t})_j$, with (C) a catalyst to form a aliphatic unsaturation premix or hydroxy premix respectively; (2") effecting a reaction by adding the aliphatic unsaturation premix or hydroxy premix to (A) at least one organohydrogen cyclosiloxane comprising at least 2 SiH bonds per molecule and having the formula

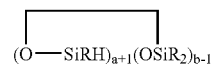

so that ratio of SiH bonds in component (A) to the aliphatic unsaturation or hydroxy group of component (B) is at least 2.5 to form a reaction mixture comprising organohydrogensilicon compounds having at least one SiH bond per molecule described by formula (I) above; (3") optionally, adding an inhibitor to the reaction mixture; and (4") optionally, isolating the organohydrogensilicon compounds; where B is boron, and A, X, R, a, b, c, d, e, f, g, h, i, j, n, o, p, q, r, s, t, u, and v are as defined above.

Each A group may be independently selected from functional groups selected from a halogen atom, an ether group, an alkoxy group, an alkoxyether group, an acyl group, an epoxy group, an amino group, or a silyl group. Examples of such functional groups represented by A are as described above for X.

Each A group may also be independently selected from hydroxy groups, monovalent hydrocarbon groups comprising 2 to 20 carbon atoms having at least one aliphatic unsaturation and monovalent oxyhydrocarbon groups comprising 2 to 20 carbon atoms having at least one aliphatic saturation. The aliphatic unsaturations of A can be found in a pendant position to the hydrocarbon chain, at the end of the hydrocarbon chain, or both, with the terminal position being preferred. Each monovalent hydrocarbon group and oxyhydrocarbon group of A can be linear, branched or cyclic and may be unsubstituted or substituted with halogen atoms. Examples of monovalent hydrocarbon groups comprising 2 to 20 carbon atoms having aliphatic unsaturation include alkenyl groups such as vinyl, allyl, 3-butenyl, 4-pentenyl, 5-hexenyl, cyclohexenyl, 6-heptenyl, 7-octenyl, 8-nonenyl, 9-decenyl, 10-undecenyl, and diene groups comprising 4 to 20 carbon atoms such as 4,7-octadienyl, 5,8-nonadienyl, 5,9-decadienyl, 6,11-dodecadienyl, 4,8-nonadienyl, and 7,13-tetradecadienyl. Examples of monovalent oxyhydrocarbon groups comprising 2 to 20 carbon atoms include alkenyloxy groups such as oxybutylvinylether and alkynyloxy groups such as propargyloxy or hexynyloxy.

Preferably, each A is independently selected from a monovalent hydrocarbon group comprising 2 to 20 carbon atoms having aliphatic unsaturation, a hydroxy group, or an epoxy group. It is more preferred for A to be an alkenyl radical, with an alkenyl radical comprising 2 to about 8 carbon atoms being most preferred for A.

The methods described above for making organohydrogensilicon compounds having at least one SiH group per molecule, are examples of some preferred methods and are not meant to describe all the various methods of making such materials. Depending on the starting materials used and the desired organohydrogensilicon compound, the initial organohydrogensilicon compound formed may be subjected to subsequent hydrosilylations and/or condensations utilizing at least one hydrocarbon, oxyhydrocarbon or functional compound having at least one aliphatic unsaturation or hydroxy group so to form the desired organohydrogensilicon compound having at least one SiH group per molecule as described by Formula (I).

The methods described above preferably further comprise step (2a), (2'a) or (2"a) adding at least one hydrocarbon, oxyhydrocarbon or functional compound having at least one aliphatic unsaturation or hydroxy group to the reaction mixture comprising organohydrogensilicon compounds having at least one SiH bond per molecule formed in step (2), (2'), or (2") respectively so to form a second reaction mixture comprising organohydrogensilicon compounds having at least one SiH bond per molecule where a certain percentage of SiH groups have been converted to hydrocarbon, oxyhydrocarbon or functional groups.

Examples of the hydrocarbon, oxyhydrocarbon and functional compounds having at least one aliphatic unsaturation or hydroxy group useful for these subsequent reactions include compounds which contain the type of groups described above for A so long as they also include either a aliphatic unsaturation or hydroxy group. Preferred compounds include functional compounds such as allylglycidyl ether and vinylcyclohexylepoxide, alkenes such as 1-hexene, 1-octene, and vinylcyclohexene and dienes such as 1,5-hexadiene.

When these subsequent reactions are utilized it is preferred that 5 to 70% of the SiH groups are replaced or converted to hydrocarbon, oxyhydrocarbon or functional groups, more preferably 5 to 50% and most preferably 10 to 30%.

The organohydrogensiloxanes of component (A) may be prepared by known methods or are commercially available. It is preferred that the organohydrogen cyclosiloxanes used in the reaction are relatively pure and substantially free from oligomeric linears. The compounds of component (B) containing at least one aliphatic unsaturation or hydroxy group may also be prepared by known methods or are commercially available.

Catalysts typically employed for hydrosilylation and/or condensation reactions are used for the reaction between components (A) and (B). It is preferred to use platinum group metal-containing catalysts. By platinum group it is meant ruthenium, rhodium, palladium, osmium, iridium and platinum and complexes thereof. Platinum group metal-containing catalysts useful in preparing the organohydrogensiloxane are the platinum complexes prepared as described by Willing, U.S. Pat. No. 3,419,593, and Brown et al, U.S. Pat. No. 5,175,325, each of which is hereby incorporated by reference to show such complexes and their preparation. Other examples of useful platinum group metal-containing catalysts can be found in Lee et al., U.S. Pat. No. 3,989,668; Chang et al., U.S. Pat. No. 5,036,117; Ashby, U.S. Pat. No. 3,159,601; Lamoreaux, U.S. Pat. No. 3,220,972; Chalk et al., U.S. Pat. No. 3,296,291; Modic, U.S. Pat. No. 3,516,946; Karstedt, U.S. Pat. No. 3,814,730; and Chandra et al., U.S. Pat. No. 3,928,629 all of which are hereby incorporated by reference to show useful platinum group metal-containing catalysts and methods for their preparation. The platinum-containing catalyst can be platinum metal, platinum metal deposited on a carrier such as silica gel or powdered charcoal, or a compound or complex of a platinum group metal. Preferred platinum-containing catalysts include chloroplatinic acid, either in hexahydrate form or anhydrous form, and or a platinum-containing catalyst which is obtained by a method comprising reacting chloroplatinic acid with an aliphatically unsaturated organosilicon compound such as divinyltetramethyldisiloxane, or alkene-platinum-silyl complexes as described in U.S. patent application Ser. No. 10/017,229, filed Dec. 7, 2001, such as $(COD)Pt(SiMeCl_2)_2$, where COD is 1,5-cyclooctadiene and Me is methyl. These alkene-platinum-silyl complexes may be prepared, for example by mixing 0.015 mole $(COD)PtCl_2$ with 0.045 mole COD and 0.0612 moles $HMeSiCl_2$.

The appropriate amount of the catalyst will depend upon the particular catalyst used. The platinum catalyst should be present in an amount sufficient to provide at least 2 parts per million (ppm), preferably 5 to 200 ppm of platinum based on total weight percent solids (all non-solvent ingredients) in the composition. It is highly preferred that the platinum is present in an amount sufficient to provide 5 to 150 weight ppm of platinum on the same basis. The catalyst may be added as a single species or as a mixture of two or more different species. Adding the catalyst as a single species is preferred.

Components (A)-(C), and any optional components can be mixed together using any suitable mixing means, such as a spatula, a drum roller, a mechanical stirrer, a three roll mill, a sigma blade mixer, a bread dough mixer, and a two roll mill.

The temperature of the reaction is not strictly specified, but generally falls within the range of about 20° to 150° C. The length of reaction time is also not critical, and is generally determined by the addition rate of controlling reagent.

Optionally, the reaction can be run using common solvents such as toluene, xylene, methylisobutylketone, and heptane.

The manner in which the reaction is conducted is important. Since it is desired to react aliphatically unsaturated groups or hydroxy groups randomly with as many SiH containing molecules as possible, the reaction may be conducted by premixing component (A) and (B) and then catalyzing the premix; by pre-catalyzing component (A) followed by controlled introduction of component (B), by precatalyzing component (B) and then add this premix to component (A), or by something in between these three extremes.

After the organohydrogensilicon compound having at least one SiH bond is prepared, an additional preferred step is to deactivate the catalyst using an inhibitor. As used herein, the term "inhibitor" means a material that retards activity of a catalyst at room temperature but does not interfere with the properties of the catalyst at elevated temperatures. It is preferred to use an inhibitor which will not impact downstream curability. These inhibitors are well known in the art and include maleates, fumarates, acetylenic alcohols, eneynes and silylated acetylenic alcohols. Examples of suitable inhibitors include ethylenically or aromatically unsaturated amides, acetylenic compounds, silylated acetylenic compounds, ethylenically unsaturated isocyanates, olefinic siloxanes, unsaturated hydrocarbon monoesters and diesters, conjugated ene-ynes, hydroperoxides, nitriles, and diaziridines.

Preferred inhibitors include acetylenic alcohols exemplified by 1-ethynyl-1-cyclohexanol, 2-methyl-3-butyn-2-ol, 2-phenyl-3-butyn-2-ol, 2-ethynyl-isopropanol, 2-ethynyl-butane-2-ol, and 3,5-dimethyl-1-hexyn-3-ol, silylated acetylenic alcohols exemplified by trimethyl(3,5-dimethyl-1-hexyn-3-oxy)silane, dimethyl-bis-(3-methyl-1-butyn-oxy)silane, methylvinylbis(3-methyl-1-butyn-3-oxy)silane, and ((1,1-dimethyl-2-propynyl)oxy)trimethylsilane, unsaturated hydrocarbon monoesters and diesters exemplified by diallyl maleate, dimethyl maleate, diethyl fumarate, diallyl fumarate, and bis-2-methoxy-1-methylethylmaleate, mono-octyl-maleate, mono-isooctylmaleate, mono-allyl maleate, mono-methyl maleate, mono-ethyl ftimarate, mono-allyl fumarate, and 2-methoxy-1-methylethylmaleate; conjugated ene-ynes exemplified by 2-isobutyl-1-butene-3-yne, 3,5-dimethyl-3-hexene-1-yne, 3-methyl-3-pentene-1-yne, 3-methyl-3-hexene-1-yne, 1-ethynylcyclohexene, 3-ethyl-3-butene-1-yne, and 3-phenyl-3-butene-1-yne, vinylcyclosiloxanes such as 1,3,5,7-tetramethyl-1,3,5,7-tetravinylcyclotetrasiloxane, and a mixture of a conjugated ene-yne as described above and a vinylcyclosiloxane as described above.

Most preferred inhibitors are diallyl maleate, bis-2-methoxy-1-methylethylmaleate, 1-ethynyl-1-cyclohexanol, and 3,5-dimethyl-1-hexyn-3-ol.

The optimal level of inhibitor used for deactivation will vary for each inhibitor. Generally, a level of 0.2-1 wt % based on total weight percent solids (all non-solvent ingredients) in the composition is desired.

Once the platinum catalyst has been deactivated, routine volatile stripping procedures can be used to remove unreacted polyorganohydrogen cyclic siloxanes and any solvent that may have been used.

The organohydrogensilicon compounds comprising at least one silicon-bonded hydrogen described by Formula (I) are useful for a variety of applications involving coupling reactions, in particular hydrosilylation reactions. Some of the uses of these organohydrogen silicon compounds include use as a crosslinking agent in the preparation of coatings such as paper or film release coatings, textile coatings or protective electronic coatings; use as a crosslinker for the curing of liquid silicone rubber (LSR) formulations and use as an SiH intermediate for the preparation of functional silicone additives and fluids.

The following examples are disclosed to further teach, but not limit, the invention, which is properly delineated by the appended claims.

Test Methods

Gas Chromatography (GC)—GC data was collected on an HP5890A equipped with an FID and a J&W Scientific 30 m by 0.25 mm i.d. DB-1 column with 0.25 micron film thickness.

Gel Permeation Chromatography (GPC)—GPC data was collected using a Waters 515 pump, a Water 717 autosampler and a Waters 2410 differential refractometer. The separation was made with two (300 mm×7.5 mm) Polymer Laboratories Plgel 5 um Mixed-C columns, preceded by a Plgel 5 um guard column. HPLC grade toluene eluent was used at 1.0 mL/min flowrate and columns and detector were heated to 45° C. An injection volume of 50 uL was used and the sample prefiltered through a 0.45 um PTFE syringe filter. Molecular weight averages were determined relative to a calibration curve ($4^{th}$ order) created using polydimethylsiloxane (PDMS) standards covering the molecular weight range of 1300-850,000.

Silicon 29 Nuclear Magnetic Spectroscopy ($^{29}$Si NMR) $^{29}$Si NMR data was collected on a Varian Mercury 300 using chloroform D solvent. The experiment was conducted with a relaxation delay of 60 sec with a gated decoupled pulse sequence using a 5 mm switchable PFG probe was used. Alternatively, the sample was run on a Mercury 400 using a Nalorac 16 mm silicon free Pulsetune® probe with 0.03 M Cr(acac)$_3$ as a relaxation reagent and gated decoupling to ensure quantitative conditions. Both used 90 degree pulsewidth and the 400 used a 12 sec relaxation delay.

SiH Measurement—The material was measured out (according to estimated SiH content) in 125 mL Erlenmeyer flask to nearest 0.01 grams and sample weight recorded. To this was added 20 mL of prepared mercuric acetate solution (4% mercury acetate powder, 96% (1:1 mixture) methanol/chloroform), the flask was then covered and swirled to mix. A blank sample (no SiH containing material added) was also prepared for comparision. After samples stood for 30 minutes, they were quenched with 20 mL of prepared calcium chloride solution (25% calcium chloride, 75% methanol). Then 10 drops of prepared phenolphthalein solution (1% phenolphthalein in ethanol) from small pipet was added. The samples were then titrated with 0.1N methanolic potassium hydroxide and measurements taken.

EXAMPLE 1

To a reaction vessel was added 2947 g of a poly(methylhydrogen) cyclic siloxane (MeH cyclics) having an average Dp of about 4.4 (49.1 moles SiH) and 5053 g of a dimethylvinylsiloxy end-blocked polydimethylsiloxane polymer having an average Dp of about 8 (14.4 moles vinyl) to give an SiH/SiVi ratio of 3.4:1. The polymers were well mixed and a vinylsiloxane diluted platinum (Pt) catalyst added to give a Pt content of about 12 ppm. An exothermic reaction was initiated and over a period of 10 minutes the temperature of the vessel contents rose from 25° C. to 137° C. After cooling for 2 hours, bis(2-methoxy-1-methylethyl)maleate (80 g, 1 wt %) was added to stabilize the Pt from further activity. The resulting polymer was not stripped and was shown by GC to have a remaining unreacted MeH cyclics content of about 4%. The isolated product had a viscosity of 78 mPa·s, a SiH level of 0.42 wt % (SiH as H) as determined by titration and a GPC Mn=2810 and Mw=8115 vs polydimethylsiloxane (PDMS) standards. $^{29}$Si NMR analysis of the product demonstrated that all vinyl functionality has been consumed yielding silethylene bridges, no ring opening has occurred and that the resulting molecular structure is consistent with a methylhydrogen cyclic siloxane capped linear siloxane polymer as described below, where Me is methyl, x is an average of 6.5 for Mw and an average of 1.5 for Mn and d is an average of about 8.

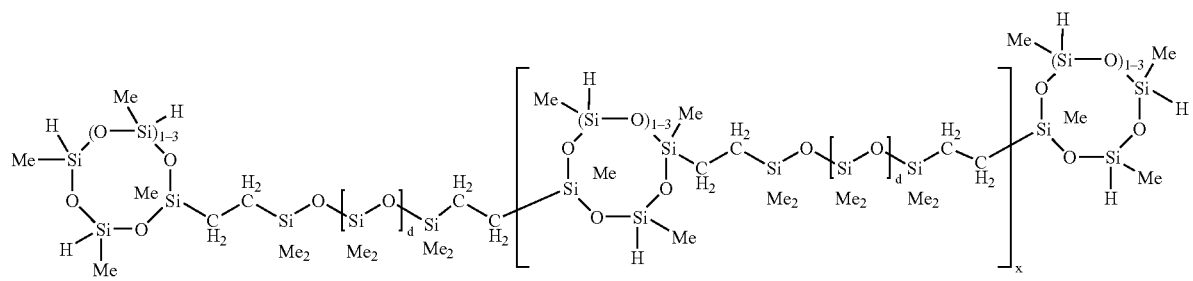

EXAMPLE 2

To a reaction vessel was added 5211 g of a poly(methylhydrogen)cyclic siloxane (MeH cyclics) having an average degree of polymerization (Dp) of about 4.4 (86.7 moles SiH) and 3340 g of a dimethylvinylsiloxy end-blocked polydimethylsiloxane having an average Dp of about 8 (9.6 moles vinyl) to give an SiH/SiVi ratio of 9:1. The polymers were well mixed and a vinylsiloxane diluted platinum (Pt) catalyst added to give a Pt content of about 12 ppm. An exothermic reaction was initiated and over a period of 10 minutes the temperature of the vessel contents rose from 23° C. to 100° C. After cooling for 30 minutes, bis(2-methoxy-1-methylethyl) maleate (60 g, 0.7 wt %) was added to stabilize the Pt from further activity. The resulting product was stripped on a rotovap at 1 mm Hg and 50° C. to remove unreacted poly(methylhydrogen)cyclic siloxane. The isolated product had a viscosity of 23 mPa·s, a SiH level of 0.58 wt % (SiH as H) as determined by titration and a GPC Mn=1396 and Mw=2753 vs PDMS standards. $^{29}$Si NMR analysis of the crosslinker product demonstrated that all vinyl functionality has been consumed yielding silethylene bridges, no ring opening has occurred and that the resulting molecular structure is consistent with a methylhydrogen cyclic siloxane capped linear siloxane polymer, where Me is methyl, x is an average of 1.5 for Mw and average of 0 for Mn, and d is an average of about 8.

EXAMPLE 3

To a reaction vessel was added 11.1 g of a poly(methylhydrogen)cyclosiloxane having an average Dp of about 4.4 and 50 g of a dimethylvinylsiloxy end-blocked polydimethylsiloxane polymer having an average Dp of about 25 to give an SiH/SiVi ratio of 3.5:1. The polymers were well mixed and a vinylsiloxane diluted Pt catalyst added to give a Pt content of about 10 ppm. The typical and expected exothermic reaction was observed. The resulting product was not stripped and was used immediately for performance evaluation without the Pt being deactivated. Titration showed that the product had an SiH level of 0.20 wt % (SiH as H). $^{29}$Si NMR analysis of the product would demonstrate that all vinyl functionality has been consumed yielding silethylene bridges, no ring opening has occurred and that the resulting molecular structure is consistent with a methylhydrogen cyclic siloxane capped linear siloxane polymer as described below, where Me is methyl, x is an average of 6.5 for Mw and an average of 1.5 for Mn and d is an average of about 8.

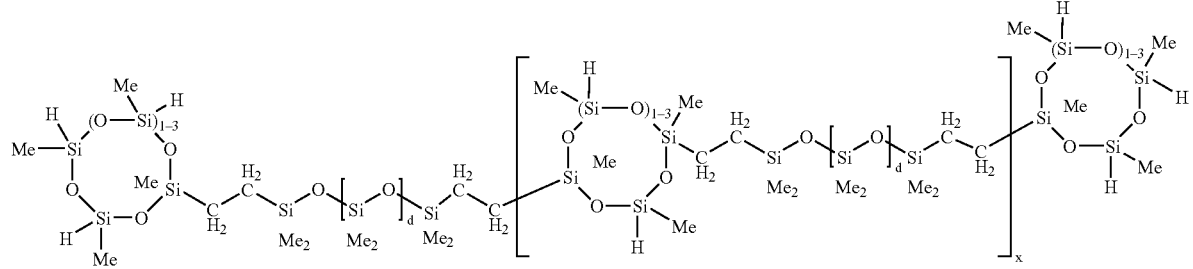

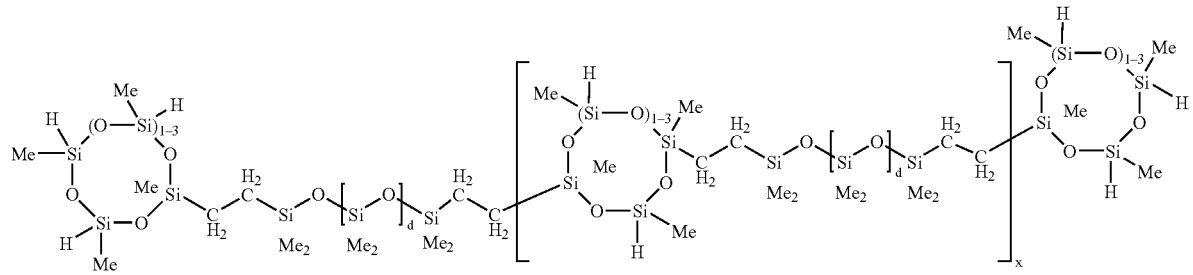

EXAMPLE 4

To a reaction vessel was added 312 g of a poly(methylhydrogen)cyclosiloxane having an average Dp of about 4.4 (5.2 mol SiH) and 3000 g of a dimethylvinylsiloxy end-blocked polydimethylsiloxane polymer having an average Dp of about 60 (1.5 mol Vi) to give an SiH/SiVi ratio of 3.5:1. The polymers were well mixed and a vinylsiloxane diluted Pt catalyst added to give a Pt content of about 10 ppm. The typical and expected exothermic reaction was observed. After cooling for 3 hours, bis(2-methoxy-1-methylethyl)maleate (0.3% by weight, 9.9 g) was added to deactivate the Pt. The resulting polymer was isolated without stripping and gave a polymer of 1350 cP with a SiH content of 0.09 wt % (SiH as H). $^{29}$Si NMR analysis of the product would demonstrate that all vinyl functionality has been consumed yielding silethylene bridges, no ring opening has occurred and that the resulting molecular structure is consistent with a methylhydrogen cyclic siloxane capped linear siloxane polymer as described below, where Me is methyl, x is an average of 6.5 for Mw and an average of 1.5 for Mn and d is an average of about 8.

EXAMPLE 5

To a reaction vessel was added 20.1 g of a poly(methylhydrogen)cyclosiloxane having an average Dp of about 4.4 (0.3 mol SiH) and 50 g of a dimethylvinylsiloxy end-blocked polydimethylsiloxane polymer having an average Dp of about 60 (0.02 mol Vi) to give an SiH/SiVi ratio of 15:1. The polymers were well mixed and a vinylsiloxane diluted Pt catalyst added to give a Pt content of about 10 ppm. The typical and expected exothermic reaction was observed. The resulting polymer was stripped on a rotary evaporator to remove volatiles and was used immediately for performance evaluation without the Pt being deactivated. Titration showed that the product had an SiH level of 0.14 wt % (SiH as H). $^{29}$Si NMR analysis of the product would demonstrate that all vinyl functionality has been consumed yielding silethylene bridges, no ring opening has occurred and that the resulting molecular structure is consistent with a methylhydrogen cyclic siloxane capped linear siloxane polymer, where Me is methyl, x is an average of 1.5 for Mw and average of 0 for Mn, and d is an average of about 8.

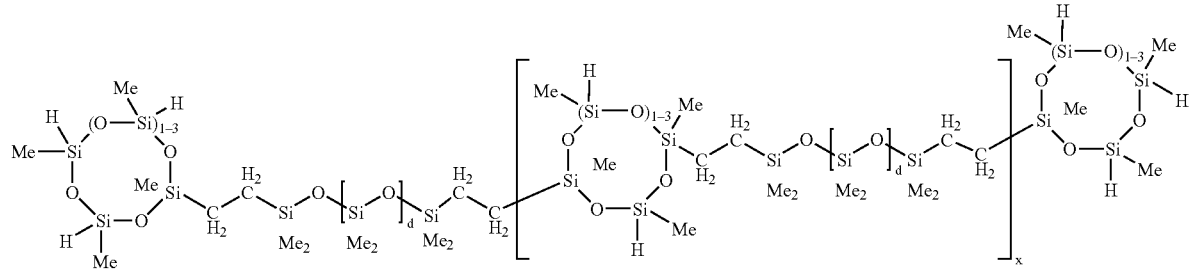

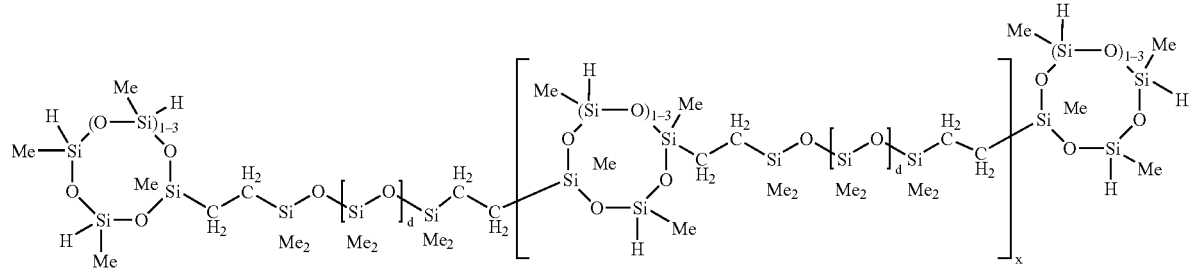

EXAMPLE 6

To a reaction vessel was added 297.1 g of a poly(methylhydrogen)cyclic siloxane (MeH cyclics) having an average Dp of about 4.4 (5.0 moles of SiH) and 155.3 g of a vinyl endblocked polymer having an average Dp of about 25 (0.15 moles vinyl) to give a SiH/SiVi ratio of 33:1. The polymers were well mixed and a vinylsiloxane diluted Platinum (Pt) catalyst added to give a Pt content of about 12 ppm. The exothermic reaction resulted in a small to moderate temperature increase. After allowing the sample to cool for a few hours, bis(2-methoxy-1-methylethyl)maleate (0.4 g, 1 wt %.) was added to stabilize the Pt from further activity. The resulting polymer was stripped on a rotovap at 1 mm Hg and 50 degrees Celsius to remove any unreacted MeH cyclics. The isolated product had a viscosity of 49 mPa·s, a SiH level of 0.28 wt % (SiH as H) as determined by titration and molecular weight as measured by GPC of Mn=2518 and Mw=33550 versus polydimethylsiloxane (PDMS) standards. $^{29}$Si and $^{13}$C NMR analysis of the product demonstrated that all vinyl functionality has been consumed yielding silethylene bridges, no ring opening had occurred and that the resulting molecular structure is consistent with a methylhydrogen cyclic siloxane capped linear siloxane polymer as described below, where Me is methyl, x corresponds to 10 for Mw, 0 for Mn and d is an average of about 25.

EXAMPLE 7

To a reaction vessel was added 279.0 g of a poly(methylhydrogen)cyclic siloxane (MeH cyclics) having an average Dp of about 4.4 (4.7 moles of SiH) and 175.0 g of 30 dp OH-endblocked polymer (0.16 mol OH) to give an SiH/SiOH ratio of 30:1. The polymers were well mixed and a vinylsiloxane diluted Platinum (Pt) catalyst added to give a Pt content of about 12 ppm. The exothermic reaction resulted in a small to moderate temperature increase. After allowing the sample to cool for a few hours, bis(2-methoxy-1-methylethyl)maleate (0.40 g, 1 wt %) was added to stabilize the Pt from further activity. The resulting polymer was stripped on a rotovap at 1 mm Hg and 50 degrees Celsius to remove any unreacted poly(methylhydrogen)cyclic siloxane. The isolated product had a viscosity of 422 mPa·s, a SiH level of 0.22 wt % (SiH as H) as determined by titration and a molecular weight as determined by GPC of Mn=5510 and Mw=65260 vs. polydimethylsiloxane (PDMS) standards. $^{29}$Si and $^{13}$C NMR analysis of the product demonstrated that all OH functionality had been consumed yielding $SiO_{3/2}$ structural units (T), no ring opening had occurred and that the resulting molecular structure is consistent with a methylhydrogen cyclic siloxane capped linear siloxane polymer as described below, where Me is methyl, x is an average of 18 for Mw, an average of 1.5 for Mn and d is an average of about 30.

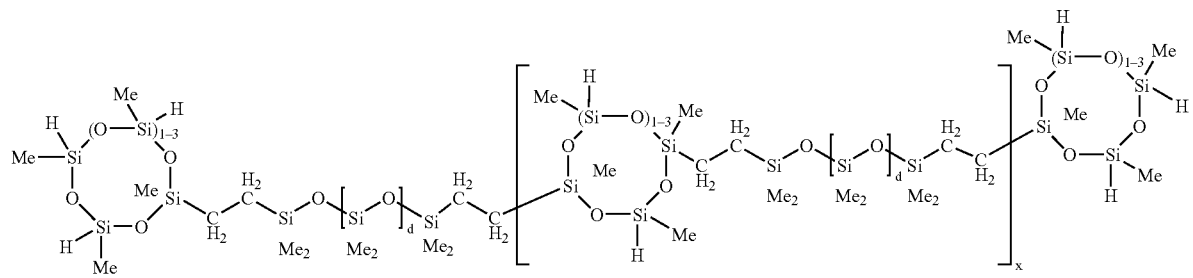

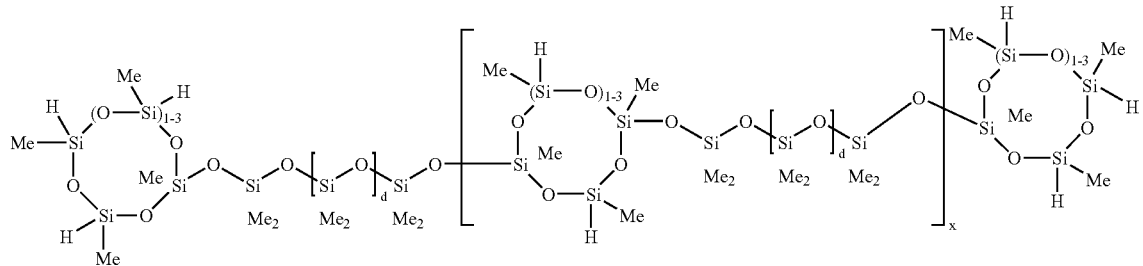

EXAMPLE 8

To a reaction vessel was added 272.6 g of a poly(methylhydrogen)cyclic siloxane (MeH cyclics) having an average Dp of about 4.4 (4.5 moles of SiH) and 175.0 g of a vinyldimethylsiloxy endblocked poly(dimethylsiloxane-silicate) copolymer having an average dp of 100 (0.093 mol vinyl) to give an SiH/SiVi ratio of 49:1. The polymers were well mixed and a vinylsiloxane diluted Platinum (Pt) catalyst added to give a Pt content of about 12 ppm. The exothermic reaction resulted in a small to moderate temperature increase. After allowing the sample to cool for a few hours, bis(2-methoxy-1-methylethyl)maleate (0.39 g, 1 wt %) was added to stabilize the Pt from further activity. The resulting polymer was stripped on a rotovap at 1 mm Hg and 50 degrees Celsius to remove any unreacted MeH cyclics. The isolated product had a viscosity of 263 mPa·s, a SiH level of 0.15 wt % (SiH as H) as determined by titration and a molecular weight as determined by GPC of Mn=5615 and Mw=30030 vs. polydimethylsiloxane (PDMS) standards. $^{29}$Si and $^{13}$C NMR analysis of the product demonstrates that all vinyl functionality had been consumed yielding silethylene bridges, no ring opening had occurred and that the resulting nominal Mn molecular structure is consistent with a methylhydrogen cyclic siloxane capped siloxane polymer as described below, where Me is methyl and d is about 25. Oligomers of this structure can of course grow from any or all of the arms.

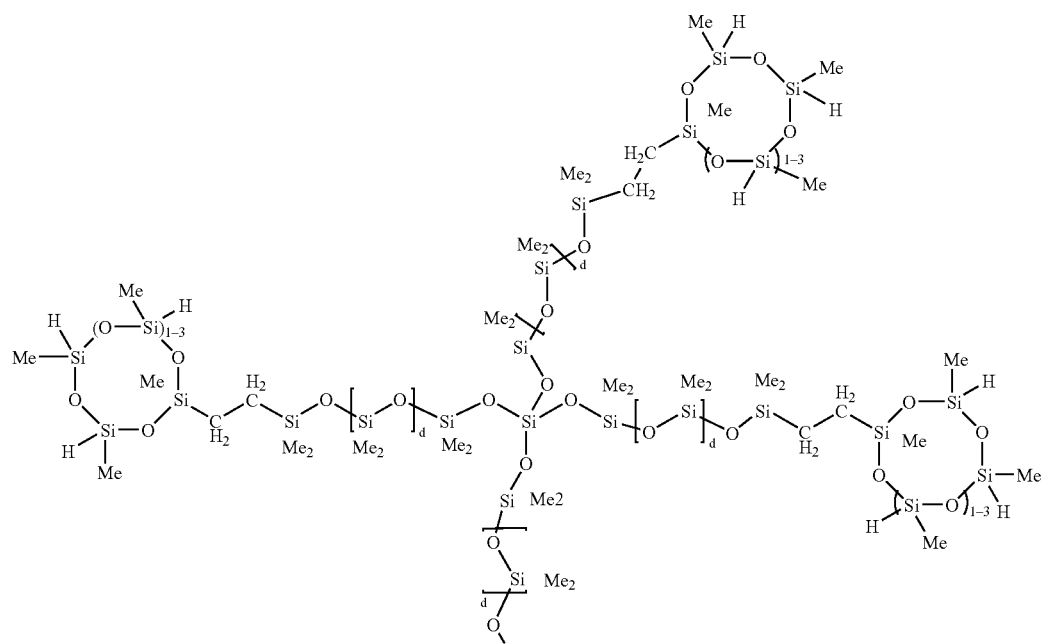

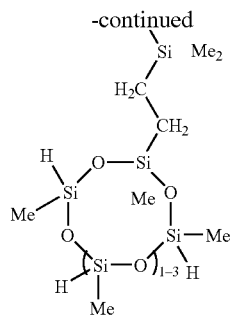

EXAMPLE 9

To a reaction vessel was added 238.2 g of a poly(methylhydrogen)cyclic siloxane (MeH cyclics) having an average Dp of about 4.4 (4.0 moles of SiH) and 175.0 g of an endblocked and vinyl pendant polydimethylsiloxane copolymer (0.08 mol vinyl) to give an SiH/SiVi ratio of 50:1. The polymers were well mixed and a vinylsiloxane diluted Platinum (Pt) catalyst added to give a Pt content of about 12 ppm. The exothermic reaction resulted in a small to moderate temperature increase. After allowing the sample to cool for a few hours, bis(2-methoxy-1-methylethyl)maleate (0.39 g, 1 wt %) was added to stabilize the Pt from further activity. The resulting polymer was stripped on a rotovap at 1 mm Hg and 50 degrees Celsius to remove any unreacted MeH cyclics. The isolated product had a viscosity of 295 mPa·s, a SiH level of 0.15 wt % (SiH as H) as determined by titration and a molecular weight as measured by GPC of Mn=6872 and Mw=21960 vs. polydimethylsiloxane (PDMS) standards. $^{29}$Si and $^{13}$C NMR analysis of the product demonstrates that all vinyl functionality had been consumed yielding silethylene bridges, no ring opening had occurred and that the resulting nominal Mn molecular structure is consistent with a methylhydrogen cyclic siloxane capped pendant and endblocked PDMS siloxane polymer as described below, where Me is methyl, $d_1$ is about 97 and $d_2$ is about 1.3. Oligomers of this structure can grow from the endblocked or pendant arms.

EXAMPLE 10

To a reaction vessel was added 236.1 g of a poly(methylhydrogen)cyclic siloxane (MeH cyclics) having an average Dp of about 4.4 (3.9 moles of SiH) and 175.0 g of an endblocked and hexenyl pendant polydimethylsiloxane copolymer (0.076 mol vinyl) to give an SiH/SiVi ratio of 52:1. The polymers were well mixed and a vinylsiloxane diluted Platinum (Pt) catalyst added to give a Pt content of about 12 ppm. The exothermic reaction resulted in a small to moderate temperature increase. After allowing the sample to cool for a few hours, bis(2-methoxy-1-methylethyl)maleate (0.39 g, 1 wt %) was added to stabilize the Pt from further activity. The resulting polymer was stripped on a rotovap at 1 mm Hg and 50 degrees Celsius to remove any unreacted poly(methylhydrogen)cyclic siloxane. The isolated product had a viscosity of 284 mPa·s, a SiH level of 0.17 wt % (SiH as H) as determined by titration and a molecular weight as determined by GPC of Mn=4282 and Mw=17290 vs. polydimethylsiloxane (PDMS) standards. $^{29}$Si and $^{13}$C NMR analysis of the product demonstrated that all vinyl functionality had been consumed yielding silethylene bridges, no ring opening had occurred and that the resulting nominal Mn molecular structure is consistent with a methylhydrogen cyclic siloxane capped endblocked and pendant siloxane polymer as described below, where Me is methyl, $d_1$ is about 97 and $d_2$ is about 1.3.

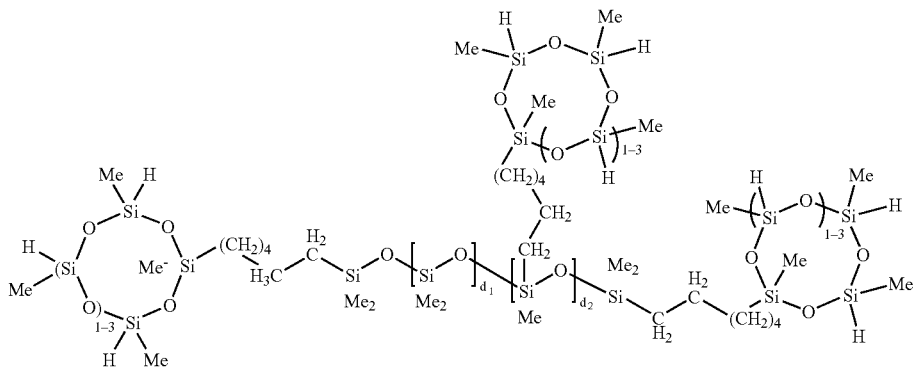

EXAMPLE 11

To a reaction vessel was added 289.7 g of a poly(methylhydrogen)cyclic siloxane (MeH cyclics) having an average Dp of about 4.4 (4.8 moles of SiH) and 175.0 g of a trimethylsiloxy endblocked, vinyl pendant polydimethylsiloxane copolymer having an average Dp of about 165 (0.089 mol vinyl) to give an SiH/SiVi ratio of 54:1. The polymers were well mixed and a vinylsiloxane diluted Platinum (Pt) catalyst added to give a Pt content of about 12 ppm. The exothermic reaction resulted in a small to moderate temperature increase. After allowing the sample to cool for a few hours, bis(2-methoxy-1-methylethyl)maleate (0.40 g, 1 wt %) was added to stabilize the Pt from further activity. The resulting polymer was stripped on a rotovap at 1 mm Hg and 50 degrees Celsius to remove any unreacted poly(methylhydrogen)cyclics. The isolated product had a viscosity of 1020 mPa·s, a SiH level of 0.19 wt % (SiH as H) as determined by titration and a molecular weight as determined by GPC of Mn=8902 and Mw=60370 vs polydimethylsiloxane (PDMS) standards. $^{29}$Si and $^{13}$C NMR analysis of the product demonstrates that all vinyl functionality had been consumed yielding silethylene bridges, no ring opening had occurred and that the resulting nominal Mn molecular structure is consistent with a methylhydrogen cyclic siloxane capped vinyl pendant siloxane polymer as described below, where Me is methyl, $d_1$ is about 157 and $d_2$ is about 6.

EXAMPLE 12

To a reaction vessel was added 233.9 g of a poly(methylhydrogen)cyclic siloxane (MeH cyclics) having an average Dp of about 4.4 (3.9 moles of SiH) and 175.0 g of a trimethylsiloxy endblocked, hexenyl pendant polydimethylsiloxane copolymer (0.076 mol vinyl) to give an SiH/SiVi ratio of 51:1. The polymers were well mixed and a vinylsiloxane diluted Platinum (Pt) catalyst added to give a Pt content of about 12 ppm. The exothermic reaction resulted in a small to moderate temperature increase. After allowing the sample to cool for a few hours, bis(2-methoxy-1-methylethyl)maleate (0.39 g, 1 wt %) was added to stabilize the Pt from further activity. The resulting polymer was stripped on a rotovap at 1 mm Hg and 50 degrees Celsius to remove any unreacted poly(methylhydrogen) cyclic. The isolated product had a viscosity of 585 mPa·s, a SiH level of 0.15 wt % (SiH as H) as determined by titration and a molecular weight as detemmined by GPC of Mn=7930 and Mw=50100 vs polydimethylsiloxane (PDMS) standards. $^{29}$Si and $^{13}$C NMR analysis of the product demonstrated that all vinyl functionality had been consumed yielding silethylene bridges, no ring opening had occurred and that the resulting nominal Mn molecular structure is consistent with a methylhydrogen cyclic siloxane capped pendant siloxane polymer as described below, where Me is methyl, $d_1$ is about 143 and $d_2$ is about 5.

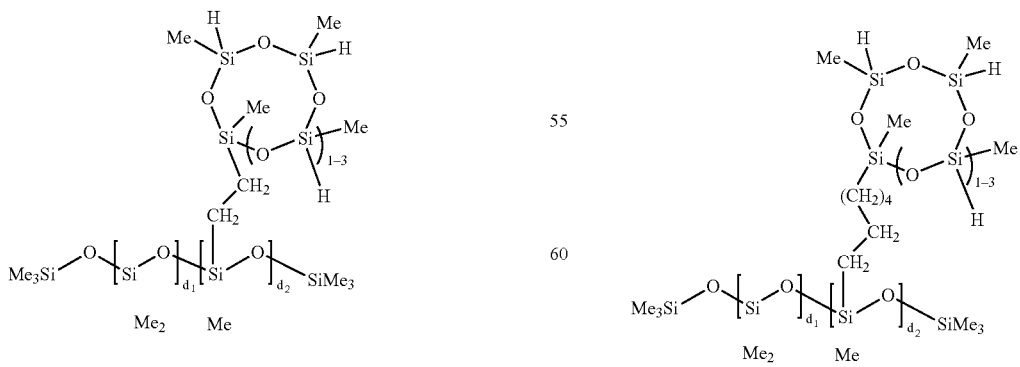

EXAMPLE 13

To a reaction vessel was added 654.0 g of a poly(methylhydrogen)cyclic siloxane (MeH cyclics) having an average Dp of about 4.4 (6.9 moles of SiH) and 110.0 g of a hexenyl endblocked polydimethylsiloxane polymer (0.25 mol vinyl) to give an SiH/SiVi ratio of 44:1. The polymers were well mixed and a vinylsiloxane diluted Platinum (Pt) catalyst added to give a Pt content of about 12 ppm. The exothermic reaction resulted in a small to moderate temperature increase. After allowing the sample to cool for a few hours, bis(2-methoxy-1-methylethyl)maleate (0.39 g, 1 wt %) was added to stabilize the Pt from further activity. The resulting polymer was stripped on a rotovap at 1 mm Hg and 50 degrees Celsius to remove any unreacted poly(methylhydrogen)cyclic siloxane. The isolated product had a viscosity of 29 mPa·s, a SiH level of 0.50 wt % (SiH as H) as determined by titration and a molecular weight as determined by GPC of Mn=1648 and Mw=16060 vs polydimethylsiloxane (PDMS) standards. $^{29}$Si and $^{13}$C NMR analysis of the product demonstrated that all vinyl functionality has been consumed yielding silethylene bridges, no ring openings had occurred and that the resulting molecular structure is consistent with a methylhydrogen cyclic siloxane capped linear siloxane polymer as described below, where Me is methyl, x corresponds to 8 for Mw, 0 for Mn and d is an average of about 10.

EXAMPLE 14

To a reaction vessel was added 837.0 g of a poly(methylhydrogen)cyclic siloxane (MeH cyclics) having an average Dp of about 4.4 (14.0 moles of SiH) and 65.0 g of tetrakis (vinyldimethylsiloxy)silane (0.60 mol vinyl) to give an SiH/SiVi ratio of 23:1. The polymers were well mixed and a vinylsiloxane diluted Platinum (Pt) catalyst added to give a Pt content of about 12 ppm. The exothermic reaction resulted in a small to moderate temperature increase. After allowing the sample to cool for a few hours, bis(2-methoxy-1-methylethyl)maleate (0.40 g, wt %) was added to stabilize the Pt from further activity. The resulting polymer was stripped on a rotovap at 1 mm Hg and 50 degrees Celsius to remove any unreacted poly(methylhydrogen)cyclic siloxane. The isolated product had a viscosity of 81 mPa·s, a SiH level of 0.90 wt % (SiH as H) as determined by titration and a molecular weight as determined by GPC of Mn=1460 and Mw=18600 vs polydimethylsiloxane (PDMS) standards. $^{29}$Si and $^{13}$C NMR analysis of the product demonstrated that all vinyl functionality has been consumed yielding silethylene bridges, no ring opening had occurred and that the resulting nominal molecular structure for Mn is consistent with a methylhydrogen cyclic siloxane capped siloxane polymer as described below, where Me is methyl. Higher oligomers can grow from any of the branches.

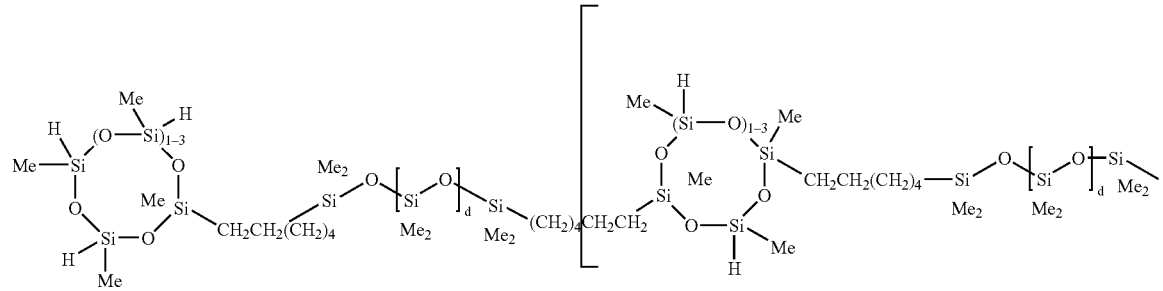

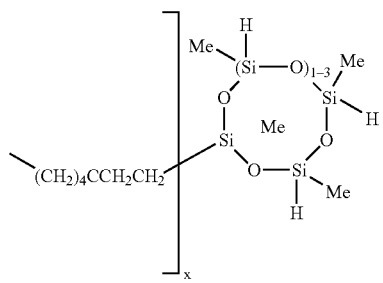

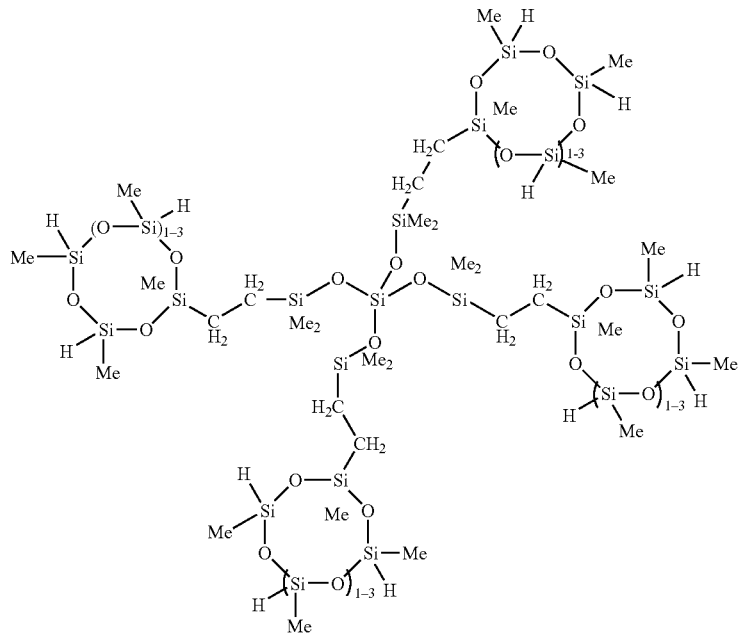

EXAMPLE 15

To a reaction vessel was added 729.7 g of a poly(methylhydrogen)cyclic siloxane (MeH cyclics) having an average Dp of about 4.4 (12.2 moles of SiH) and 85.0 g of tetrakis(hexenyldimethylsiloxy)silane (0.52 mol vinyl) to give an SiH/SiVi ratio of 24:1. The polymers were well mixed and a vinylsiloxane diluted Platinum (Pt) catalyst added to give a Pt content of about 12 ppm. The exothermic reaction resulted in a small to moderate temperature increase. After allowing the sample to cool for a few hours, bis(2-methoxy-1-methylethyl)maleate (0.40 g, wt %) was added to stabilize the Pt from further activity. The resulting polymer was stripped on a rotovap at 1 mm Hg and 50 degrees Celsius to remove any unreacted poly(methylhydrogen)cyclic. The isolated product had a viscosity of 32 mPa·s, a SiH level of 0.70 wt % (SiH as H) as determined by titration and a molecular weight as determined by GPC of Mn=1453 and Mw=27690 vs polydimethylsiloxane (PDMS) standards. $^{29}$Si and $^{13}$C NMR analysis of the product demonstrated that all vinyl functionality has been consumed yielding silethylene bridges, no ring opening had occurred and that the resulting nominal molecular structure for Mn is consistent with a methylhydrogen cyclic siloxane capped siloxane polymer as described below, where Me is methyl. Higher oligomers can grow from any of the branches.

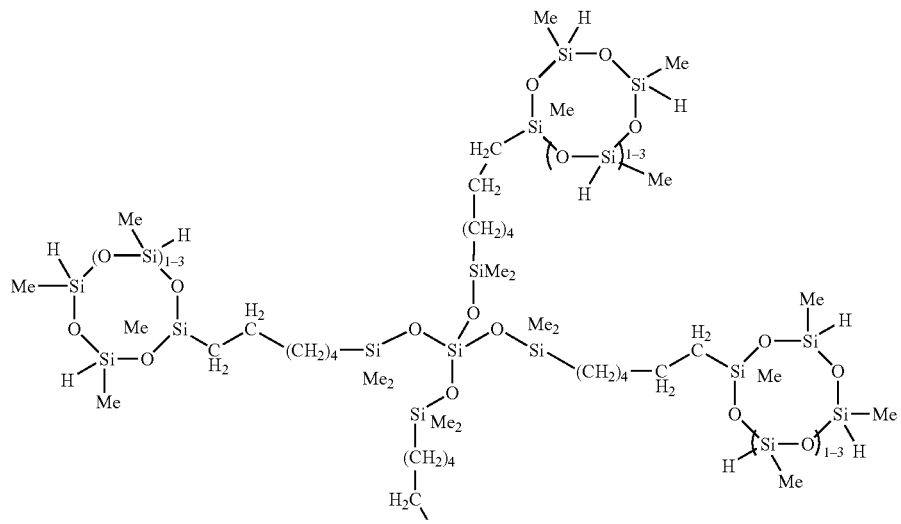

-continued

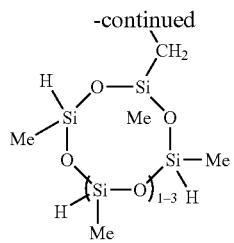

EXAMPLE 16

To a reaction vessel was added 381.1 g of a poly(methylhydrogen)cyclic siloxane (MeH cyclics) having an average Dp of about 4.4 (6.3 moles SiH) and 80.0 g of a dimethylvinylsiloxy end-blocked polydimethylsiloxane polymer having an average Dp of about 7 (0.29 moles vinyl) to give an SiH/SiVi ratio of about 22:1. The polymers were well mixed and a vinylsiloxane diluted platinum (Pt) catalyst was added to give a Pt content of 15 about 4 ppm. An exotherm reaction was initiated and over a period of 10 minutes the temperature of the vessel contents rose to above room temperature. After cooling for 2 hours, the resulting polymer was stripped in a rotovap at 1 mm Hg and 95 C to remove any unreacted poly(methylhydrogen)cyclic siloxane. The material was then allowed to cool to room temperature. After cooling, 150 g of above product was added to another reaction vessel. Then 24.3 g (0.29 moles vinyl) of 1-hexene was slowly added to the reaction vessel. An exothermic reaction was initiated with each small addition. After cooling for 2 hours, bis(2-methoxy-1-methylethyl)maleate (0.87 g, 0.5 wt %) was added to stabilize the Pt from further activity. The resulting polymer was then stripped a second time in a rotovap at 1 mm Hg and 95 C to remove any unreacted 1-hexene. After cooling to room temperature, bis(2-methoxy-1-methylethyl)maleate (0.87 g, 0.5 wt %) was added to stabilize the Pt from further activity. The material was then allowed to cool to room temperature. The isolated product had a viscosity of 62 mPa·s, a SiH level of 0.32% (SiH as H) as determined by titration and a GPC Mn=1723 and Mw=15640 versus polydimethylsiloxane (PDMS) standards. $^{29}$Si NMR analysis of the product demonstrates that all vinyl functionality has been consumed yielding silethylene bridges, no ring openings has occurred and that the resulting molecular structure is consistent with a methylhydrogen cyclic siloxane capped linear siloxane polymer as described below, where x is about 1 for Mn, about 9 for Mw and d is an average of about 7.

EXAMPLE 17

To a reaction vessel was added 737 g of a poly(methylhydrogen)cyclic siloxane (MeH cyclics) having an average Dp of about 4.4 (12.2 moles SiH) and 1263 g of a dimethylvinylsiloxy end-blocked polydimethylsiloxane polymer having an average Dp of about 8 (3.6 moles vinyl) to give an SiH/SiVi ratio of 3.4:1. The polymers were well mixed and a vinylsiloxane diluted platinum (Pt) catalyst added to give a Pt content of about 4 ppm. An exothermic reaction was initiated and over a period of 10 minutes the temperature of the vessel contents rose from 25° C. to 137° C. After the reaction mixture had cooled to 25 C, 91.1 g (0.80 mol) allylglycidylether (AGE) was added. The reaction was then heated via heating mantle to 50 C at which point the heat was turned off. The reaction mixture continued to exotherm to 66 C over 5 minutes and held steady at 66 C for an additional 5 minutes. Analysis by gas chromatography at this point showed no trace of the AGE raw material. When the temperature began to drop, the heat was turned back on and the reaction mixture was maintained at 80 C for 2 hours. The reaction was then allowed to cool to 25 C. To stabilize the product, 4.2 g (0.2 wt. %) bis(2-methoxy-1-methylethyl)maleate was then added. The isolated product had a viscosity of 93 mPa·s, a SiH level of 0.36% (SiH as H) as determined by titration and a GPC Mn=2626 and Mw=6405 versus polydimethylsiloxane (PDMS) standards. The structure is shown below, where 10% of the SiH functions have been replaced with a propylglycidylether group, x=1-5 and d about 8.

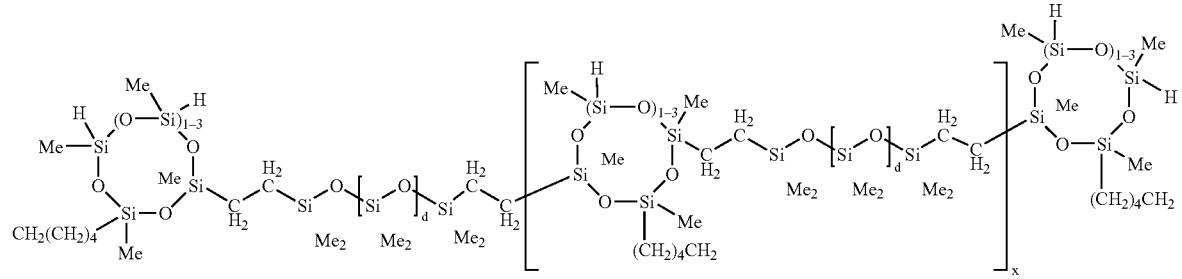

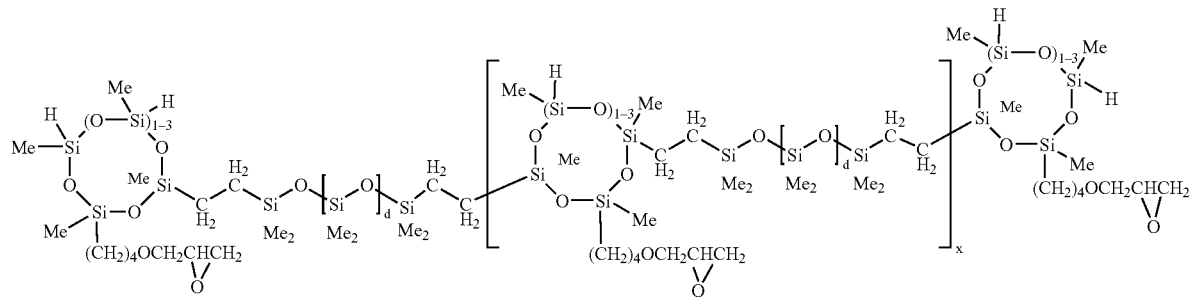

EXAMPLE 18

To a reaction vessel was added 737.0 g of a poly(methylhydrogen)cyclic siloxane (MeH cyclics) having an average Dp of about 4.4 (12.2 moles SiH) and 1263.0 g of a dimethylvinylsiloxy end-blocked polydimethylsiloxane polymer having an average Dp of about 8 (3.6 moles vinyl) to give an SiH/SiVi ratio of 3.4:1. The polymers were well mixed and a vinylsiloxane diluted platinum (Pt) catalyst added to give a Pt content of about 4 ppm. An exothermic reaction was initiated and over a period of 10 minutes the temperature of the vessel contents rose from 25° C. to 137° C. After the reaction mixture had cooled to 25 C, 227.9 g (2.0 mol) AGE was added. The reaction was then heated via heating mantle to 50 C at which point the heat was turned off. The reaction mixture continued to exotherm to 91 C over 10 minutes. Analysis by gas chromatography at this point showed no trace of the AGE raw material. When the reaction temperature had dropped back to 80 C, the heat was turned back on and the reaction mixture was maintained at 80 C for 2 hours. The reaction was then allowed to cool to 25 C. To stabilize the product, 4.2 g (0.2 wt. %) bis(2-methoxy-1-methylethyl)maleate was then added. The isolated product had a viscosity of 85 mPa·s, a SiH level of 0.30% (SiH as H) as determined by titration and a GPC Mn=2867 and Mw=7561 versus polydimethylsiloxane (PDMS) standards. The structure is shown below, where 25% of the SiH functions have been replaced with a propylglycidylether group, x=1-5 and d=about 8.

The invention claimed is:

1. Organohydrogensilicon compounds containing at least one silicon-bonded hydrogen atom per molecule described by formula (I)

(I)

where each R is independently selected from a hydrogen atom and a monovalent hydrocarbon group comprising 1 to 20 carbon atoms which is free from aliphatic unsaturation, a is an integer from 1 to 18, b is an integer from 1 to 19, a+b is an integer from 3 to 20, each X is an independently selected functional group selected from a halogen atom, an ether group, an alkoxy group, an alkoxyether group, an acyl group, an epoxy group, an amino group, a silyl group, or a -Z-$R^4$ group, where each Z is independently selected from an oxygen and a divalent hydrocarbon group comprising 2 to 20 carbon atoms, each $R^4$ group is independently selected from —$BR_uY_{2-u}$, or a group described by formula (II):

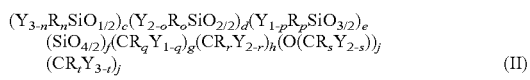
(II)

where B refers to boron, each R is as described above, the sum of c+d+e+f+g+h+i+j is at least 2, n is an integer from 0 to 3,

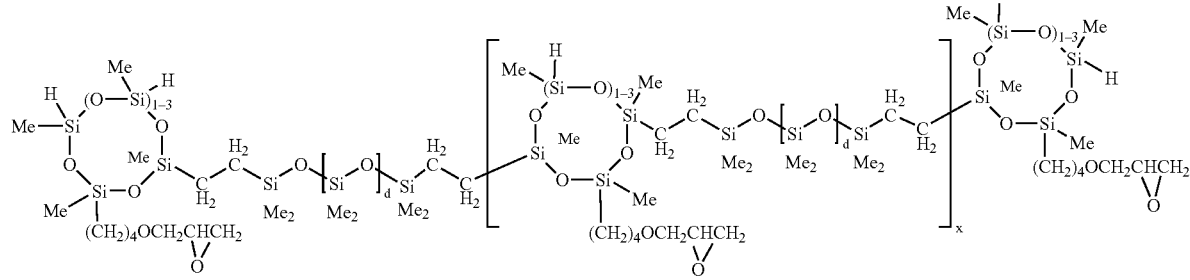

o is an integer from 0 to 2, p is an integer from 0 to 1, q is an integer from 0 to 1, r is an integer from 0 to 2, s is an integer from 0 to 2, t is an integer from 0 to 3, u is an integer from 0 to 2, each Y is an independently selected functional group selected from a halogen atom, an ether group, an alkoxy group, an alkoxyether group, an acyl group, an epoxy group, an amino group, a silyl group, or a Z-G group, where Z is as described above, each G is a cyclosiloxane described by formula (III):

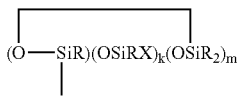
(III)

where R and X are as described above, k is an integer from 0 to 18, m is an integer from 0 to 18, k+m is an integer from 2 to 20, provided in formula (II) that one of the Y groups is replaced by the Z group bonding the $R^4$ group to the cyclosiloxane of formula (I), and provided further (a) at least one X group of Formula (I) is a -Z-$R^4$ group, (b) if Z is a divalent hydrocarbon group, a=1, c=2, e+f+g+h+i+j=0 and d>0, then at least one d unit (i.e. $Y_{2-o}R_oSiO_{2/2}$) contain a -Z-G group or the c units (i.e. $Y_{3-n}R_nSiO_{1/2}$) have no -Z-G group or at least two -Z-G groups, (c) if Z is a divalent hydrocarbon group, a=1, c=2 and d+e+f+g+h+i+j=0, then the c units (i.e. $Y_{3-n}R_n$-$SiO_{1/2}$) have no -Z-G group or at least two -Z-G groups, and (d) if g+h+i+j>0 then c+d+e+f>0.

2. The organohydrogensilicon compounds of claim 1 where subscript b is an integer from 2 to 19, subscript c is an integer from 0 to 50, subscript d is an integer from 0 to 5000, subscript e is an integer from 0 to 48, subscript f is an integer from 0 to 24, subscript g is an integer from 0 to 50, subscript h is an integer from 0 to 50, subscript i is an integer from 0 to 50, and subscript j is an integer from 0 to 50.

3. The organohydrogen silicon compounds of claim 1 where subscript c is an integer from 2 to 15, subscript d is an integer from 0 to 1000, subscript e is an integer from 0 to 13, subscript f is an integer from 0 to 6, subscript g is an integer from 0 to 20, subscript h is an integer from 0 to 20, subscript i is an integer from 0 to 20, subscript j is an integer from 0 to 15.

4. The organohydrogensilicon compounds of claim 1 where each R group is independently selected from hydrogen atoms, alkyl groups comprising 1 to 8 carbon atoms, or aryl groups comprising 6 to 9 carbon atoms, each X is a Z-$R^4$ group or is independently selected from chloro, methoxy, isopropoxy, and groups derived by hydrosilylation of the alkenyl group from hydroxybutylvinyl ether, vinylcyclohexylepoxide, and allylglycidylether with an SiH from the siloxane precursor to formulas (I) or (II), where Z is a divalent hydrocarbon group, and $R^4$ is selected from —$R_2$SiO($R_2$SiO)$_d$Si$R_2$-Z-G, —$R_2$SiOSi$R_3$, —$R_2$SiOSi$R_2$—Y, —RSi(OSi$R_3$)$_2$, where d is an integer from 1 to 50 and Z, G, and R are as described above.

5. The organohydrogensilicon compounds of claim 1 where each R group is independently selected from hydrogen, methyl, alpha-methylstyryl, 3,3,3-trifluoropropyl and nonafluorobutylethyl.

6. The organohydrogensilicon compounds of claim 1 where R is methyl, and d is an average of 8.

7. The organohydrogensilicon compounds of claims 1 where such compounds are described by the structure below where Me is methyl, d is an average of 8, and x is an integer from 1 to 15:

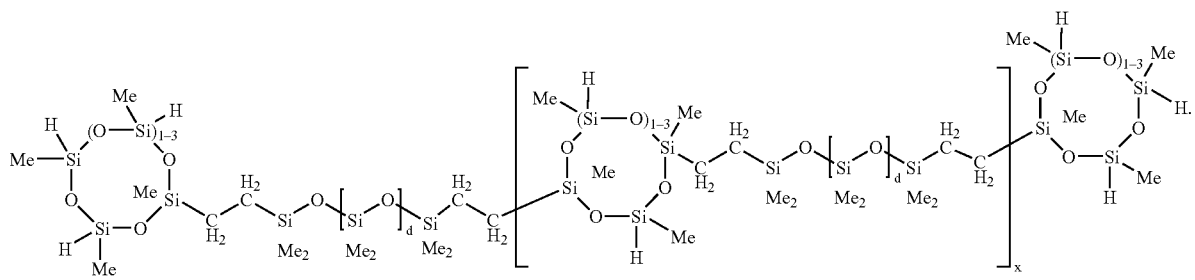

8. The organohydrogensilicon compounds of claim 7 where 10 to 30 percent of the SiH bonds are replaced by functional groups derived by hydrosilylation of allylglycidyl ether.
9. The organohydrogensilicon compounds of claim 1 where such compounds are selected from the structures below where Me is methyl, $d_1+d_2=d$, and x is an integer from 1 to 100:
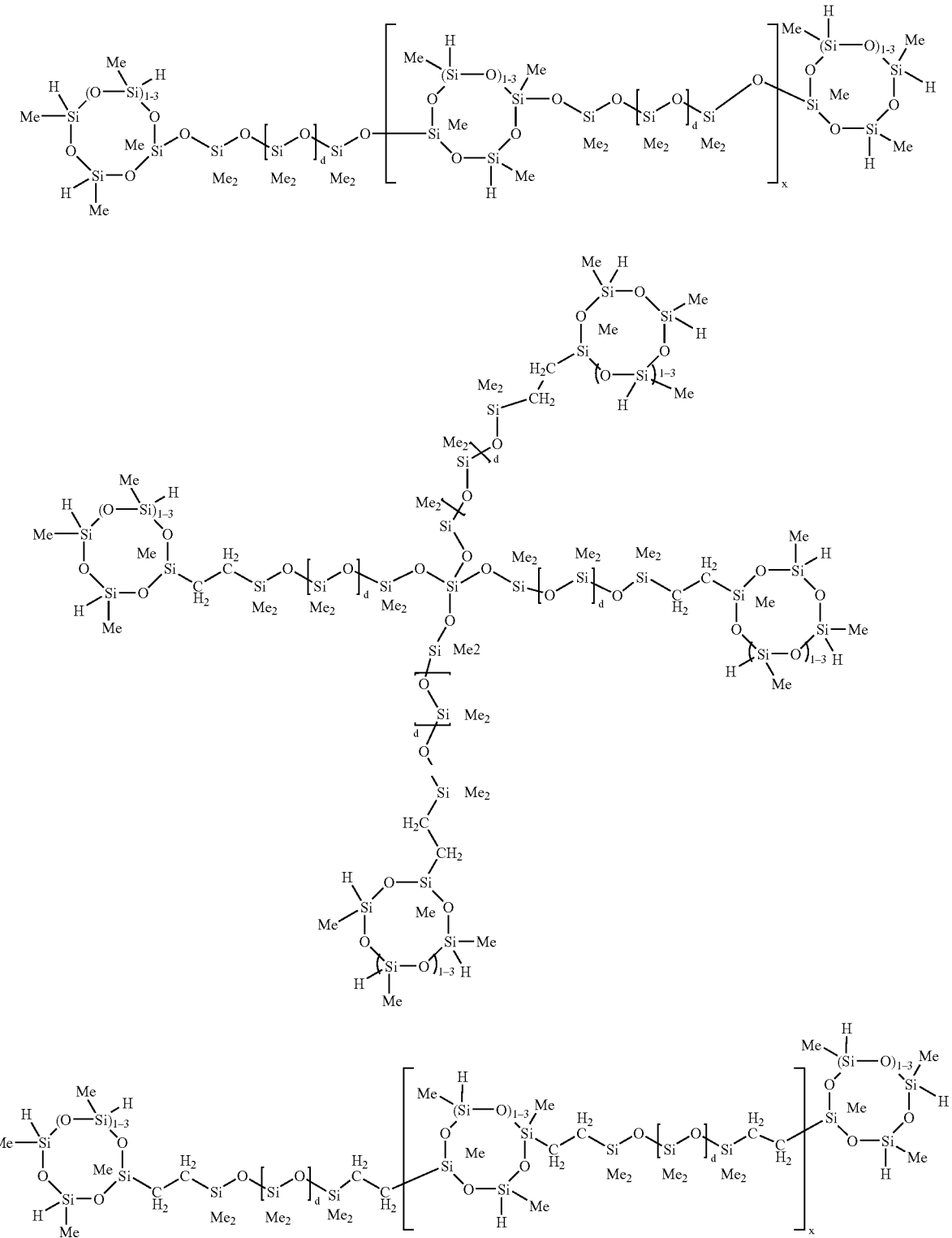

-continued
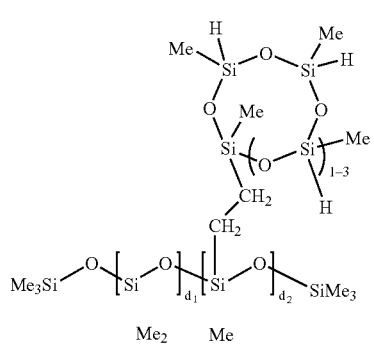 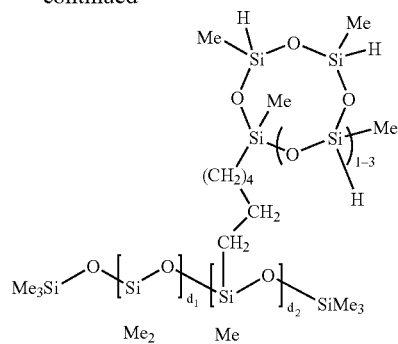
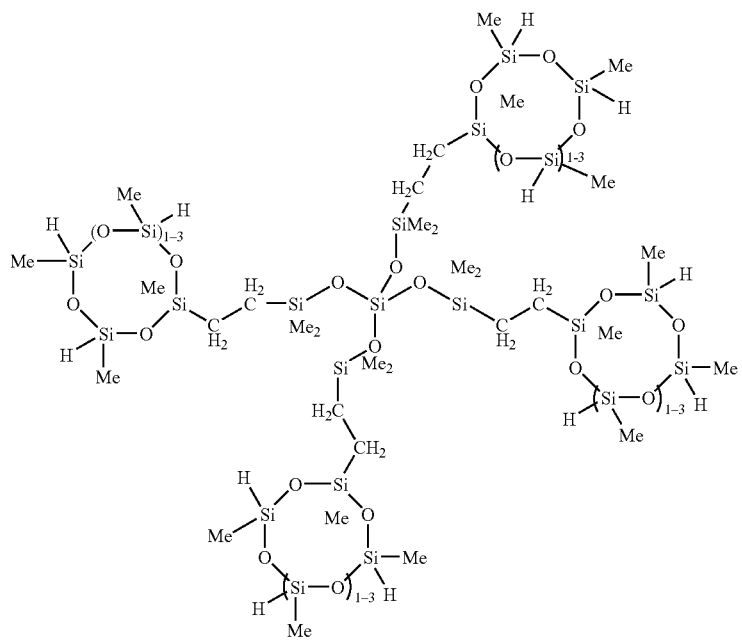
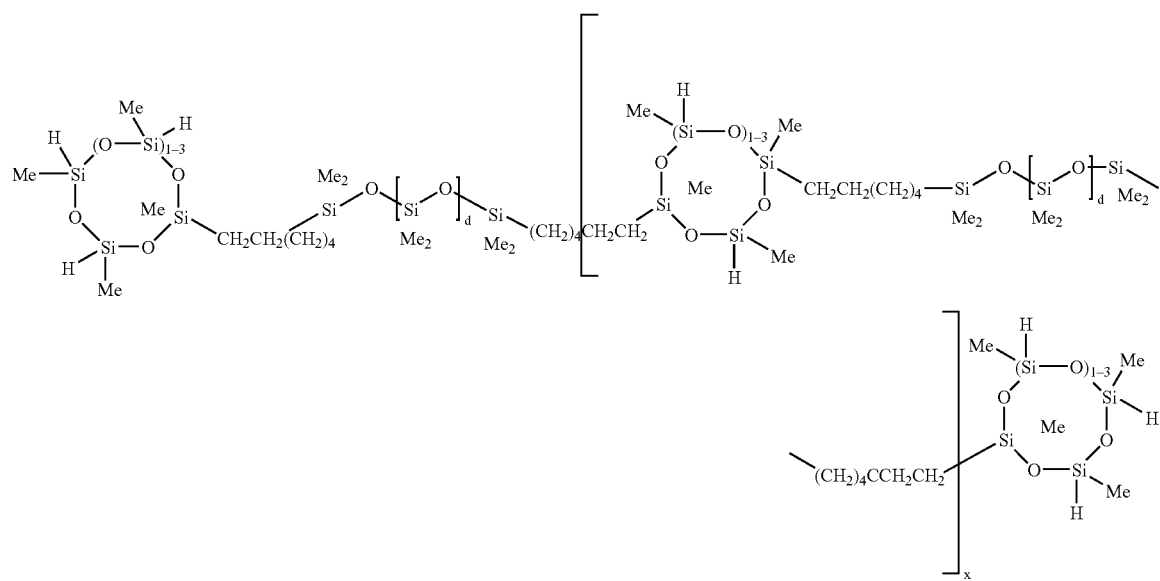

-continued
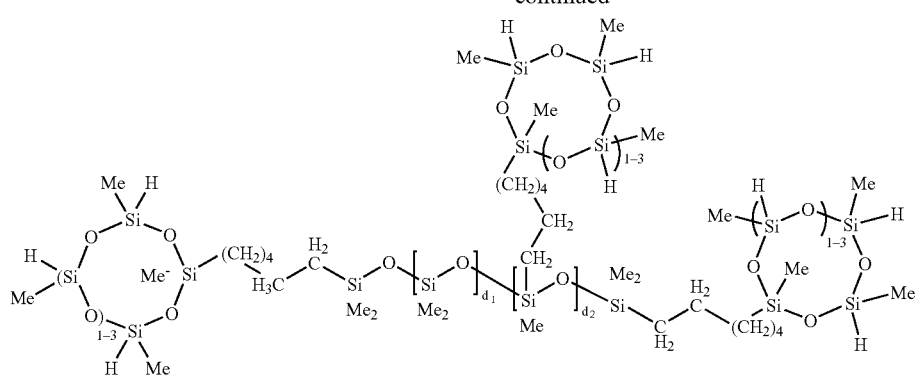
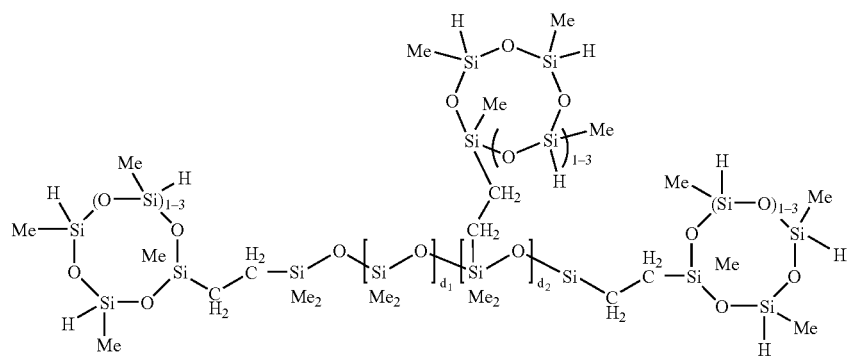
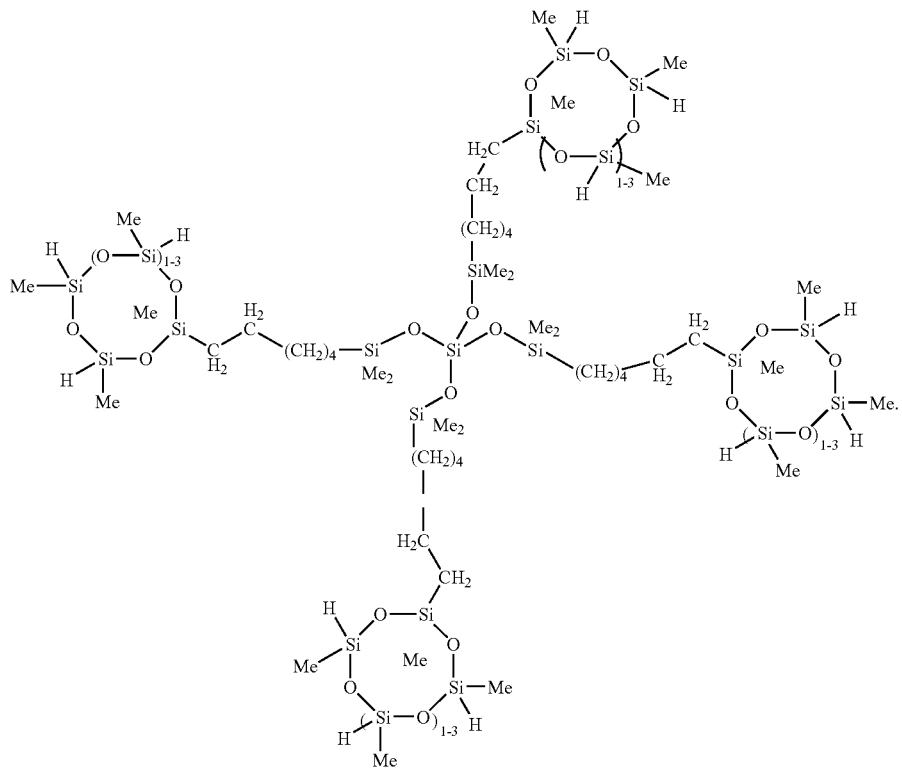

10. The organohydrogensilicon compounds of claim 9 where 5 to 70 percent of the SiH bonds are replaced by hydrocarbon, oxyhydrocarbon or functional groups.

11. The organohydrogensilicon compounds of claims 9 where 5 to 50 percent of the SiH bonds are replaced by functional groups derived by hydrosilylation of allylglycidyl ether(propylglycidyl ether groups) or vinylcyclohexylepoxide, alkyl groups or alkenyl groups.

12. The organohydrogensilicon compounds of claim 9 where 10 to 30 percent of the SiH bonds are replaced by functional groups derived by hydrosilylation of allylglycidyl ether(propylglycidyl ether groups).

13. The organohydrogensilicon compounds of claim 1 where such organohydrogensilicon compounds contain at least 2 silicon-bonded hydrogen atoms per molecule.

14. The method of claim 13 where subscript b is 2 to 19.

15. The organohydrogensilicon compounds of claim 1 where such organohydrogensilicon compounds contain at least 3 silicon-bonded hydrogen atoms per molecule.

16. The organohydrogensilicon compounds of claim 1 where such compounds have a viscosity from 5 to 50,000 mPa·s.

17. A method of preparing organohydrogensilicon compounds having at least one silicon-bonded hydrogen comprising (1) mixing (A) at least one organohydrogen cyclosiloxane comprising at least 2 SiH bonds per molecule and having the formula

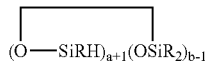

with (B) at least one compound comprising at least one aliphatic unsaturation or at least one hydroxy group per molecule described by $BR_uA_{3-u}$, or a group described by formula $(A_{3-n}R_nSiO_{1/2})_c(A_{2-o}R_oSiO_{2/2})_d(A_{1-p}R_pSiO_{3/2})_e(SiO_{4/2})_f$ $(CR_qA_{1-q})_g(CR_rA_{2-r})_h(O(CR_sA_{2-s}))_i(CR_tA_{3-t})_j$ so that the ratio of SiH bonds in component (A) to the aliphatic unsaturation or hydroxy group of component (B) is at least 2.5:1; (2)effecting a reaction between components (A) and (B) in the presence of (C) a catalyst to form a reaction mixture comprising organohydrogensilicon compounds having at least one SiH bond per molecule described by formula (I)

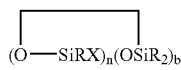 (I)

(3) optionally, adding an inhibitor to the reaction mixture; and (4) optionally, isolating the organohydrogen silicon compounds; where each R is independently selected from a hydrogen atom and a monovalent hydrocarbon group comprising 1 to 20 carbon atoms which is free from aliphatic unsaturation, a is an integer from 1 to 18, b is an integer from 1 to 19, a+b is an integer from 3 to 20, each X is an independently selected functional group selected from a halogen atom, an ether group, an alkoxy group, an alkoxyether group, an acyl group, an epoxy group, an amino group, a silyl group, or a $-Z-R^4$ group, where each Z is independently selected from an oxygen and a divalent hydrocarbon group comprising 2 to 20 carbon atoms, each $R^4$ group is independently selected from $—BR_uY_{2-u}$, or a group described by formula (II):

$(Y_{3-n}R_nSiO_{1/2})_c(Y_{2-o}R_oSiO_{2/2})_d(Y_{1-p}R_pSiO_{3/2})_e$
$(SiO_{4/2})_f(CR_qY_{1-q})_g(CR_rY_{2-r})_h(O(CR_sY_{2-s}))_j$
$(CR_tY_{3-t})_j$ (II)

where B refers to boron, each R is as described above, the sum of c+d+e+f+g+h+i+j is at least 2, n is an integer from 0 to 3, o is an integer from 0 to 2, p is an integer from 0 to 1, q is an integer from 0 to 1, r is an integer from 0 to 2, s is an integer from 0 to 2, t is an integer from 0 to 3, u is an integer from 0 to 2, each A is independently selected from a hydroxy group, a monovalent hydrocarbon group comprising 2 to about 20 carbon atoms having at least one aliphatic unsaturation, a monovalent oxyhydrocarbon group comprising 2 to about 20 carbon atoms having at least one aliphatic unsaturation, or a functional group selected from a halogen atom, an ether group, an alkoxy group, an alkoxyether group, an acyl group, an epoxy group, an amino group, a silyl group, provided at least one A group has an aliphatic unsaturation or a hydroxy group, each Y is an independently selected functional group selected from a halogen atom, an ether group, an alkoxy group, an alkoxyether group, an acyl group, an epoxy group, an amino group, or a silyl group, or a Z-G group, where Z is as described above, each G is a cyclosiloxane described by formula (III):

 (III)

where R and X are as described above, k is an integer from 0 to 18, m is an integer from 0 to 18, k+m is an integer from 2 to 20, provided in formula (II) that one of the Y groups is replaced by the Z group bonding the $R^4$ group to the cyclosiloxane of formula (I), and provided further (a) at least one X group of Formula (I) is a $-Z-R^4$ group, (b) if Z is a divalent hydrocarbon group, a=1, c=2, e+f+g+h+i+j=0 and d>0, then at least one d unit (i.e. $Y_{2-o}R_oSiO_{2/2}$) contain a -Z-G group or the c units (i.e. $Y_{3-n}R_nSiO_{1/2}$) have no -Z-G group or at least two -Z-G groups, (c) if Z is a divalent hydrocarbon group, a=1, c=2 and d+e+f+g+h+i+j=0, then the c units (i.e. $Y_{3-n}R_n$-$SiO_{1/2}$) have no -Z-G group or at least two -Z-G groups, and (d) if g+h+i+j>0 then c+d+e+f>0.

18. The method of claim 17 further comprising step (2a) adding at least one hydrocarbon, oxyhydrocarbon or functional compound having at least one aliphatic unsaturation or hydroxy group to the reaction mixture comprising organohydrogensilicon compounds having at least one SiH bond per molecule formed in step 2 so to form a second reaction mixture comprising organohydrogensilicon compounds having at least one SiH bond per molecule where 5 to 70% of the SiH bonds have been converted to a hydrocarbon, oxyhydrocarbon or functional group.

19. The method of claim 18 where the hydrocarbon, oxyhydrocarbon or functional compound having at least one aliphatic unsaturation or hydroxy group is allylglycidylether.

20. A method of preparing organohydrogensilicon compounds having at least one silicon-bonded hydrogen comprising (1') mixing (A) at least one organohydrogen cyclosiloxane comprising at least 2 SiH bonds per molecule and having the formula

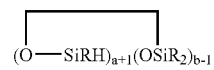

with (C) a catalyst to form a SiH premix; (2') effecting a reaction by adding to the SiH premix (B) at least one compound comprising at least one aliphatic unsaturation or at least one hydroxy group per molecule described by $BR_uA_{3-u}$, or a group described by formula $(A_{3-n}R_nSiO_{1/2})_c(A_{2-o}R_oSiO_{2/2})_d(A_{1-p}R_pSiO_{3/2})_e(SiO_{4/2})_f(CR_qA_{1-q})_g(CR_rA_{2-r})_h(O(CR_sA_{2-s}))_i(CR_tA_{3-t})_j$ so that ratio of SiH bonds in component (A) to the aliphatic unsaturation or hydroxy group of component (B) is at least 2.5 to form a reaction mixture comprising organohydrogensilicon compounds having at least one SiH bond per molecule described by formula (I)

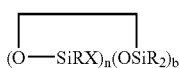  (I)

(3') optionally, adding an inhibitor to the reaction mixture; and (4') optionally, isolating the organohydrogensilicon compounds; where B is boron, each R is independently selected from a hydrogen atom and a monovalent hydrocarbon group comprising 1 to 20 carbon atoms which is free from aliphatic unsaturation, a is an integer from 1 to 18, b is an integer from 1 to 19, a+b is an integer from 3 to 20, each X is an independently selected functional group selected from a halogen atom, an ether group, an alkoxy group, an alkoxyether group, an acyl group, an epoxy group, an amino group, a silyl group, or a $-Z-R^4$ group, where each Z is independently selected from an oxygen and a divalent hydrocarbon group comprising 2 to 20 carbon atoms, each $R^4$ group is independently selected from $-BR_uY_{2-u}$, or a group described by formula (II):

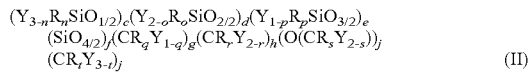  (II)

where B refers to boron, each R is as described above, the sum of c+d+e+f+g+h+i+j is at least 2, n is an integer from 0 to 3, o is an integer from 0 to 2, p is an integer from 0 to 1, q is an integer from 0 to 1, r is an integer from 0 to 2, s is an integer from 0 to 2, t is an integer from 0 to 3, u is an integer from 0 to 2, each A is independently selected from a hydroxy group, a monovalent hydrocarbon group comprising 2 to about 20 carbon atoms having at least one aliphatic unsaturation, a monovalent oxyhydrocarbon group comprising 2 to about 20 carbon atoms having at least one aliphatic unsaturation, or a functional group selected from a halogen atom, an ether group, an alkoxy group, an alkoxyether group, an acyl group, an epoxy group, an amino group, or a silyl group, provided at least one A group has an aliphatic unsaturation or a hydroxy group, each Y is an independently selected functional group selected from a halogen atom, an ether group, an alkoxy group, an alkoxyether group, an acyl group, an epoxy group, an amino group, a silyl group, or a Z-G group, where Z is as described above, each G is a cyclosiloxane described by formula (III):

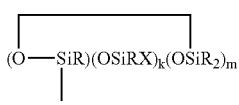  (III)

where R and X are as described above, k is an integer from 0 to 18, m is an integer from 0 to 18, k+m is an integer from 2 to 20, provided in formula (II) that one of the Y groups is replaced by the Z group bonding the $R^4$ group to the cyclosiloxane of formula (I), and provided further (a) at least one X group of Formula (I) is a $-Z-R^4$ group, (b) if Z is a divalent hydrocarbon group, a=1, c=2, e+f+g+h+i+j=0 and d>0, then at least one d unit (i.e. $Y_{2-o}R_oSiO_{2/2}$) contain a -Z-G group or the c units (i.e. $Y_{3-n}R_nSiO_{1/2}$) have no -Z-G group or at least two -Z-G groups, (c) if Z is a divalent hydrocarbon group, a=1, c=2 and d+e+f+g+h+i+j=0, then the c units (i.e. $Y_{3-n}R_nSiO_{1/2}$) have no -Z-G group or at least two -Z-G groups, and (d) if g+h+i+j>0 then c+d+e+f>0.

21. The method of claim 20 further comprising step (2'a) adding at least one hydrocarbon, oxyhydrocarbon or functional compound having at least one aliphatic unsaturation or hydroxy group to the reaction mixture comprising organohydrogensilicon compounds having at least one SiH bond per molecule formed in step 2' so to form a second reaction mixture comprising organohydrogensilicon compounds having at least one SiH bond per molecule where 5 to 70% of the SiH bonds have been converted to a hydrocarbon, oxyhydrocarbon or functional group.

22. The method of claim 21 where the hydrocarbon, oxyhydrocarbon or functional compound having at least one aliphatic unsaturation or hydroxy group is allylglycidylether.

23. A method of preparing organohydrogensilicon compounds having at least one silicon-bonded hydrogen comprising (1") mixing (B) at least one compound comprising at least one aliphatic unsaturation or at least one hydroxy group per molecule described by $BR_uA_{3-u}$, or a group described by formula $(A_{3-n}R_nSiO_{1/2})_c(A_{2-o}R_oSi_{2/2})_d(A_{1-p}R_pSiO_{3/2})_e(SiO_{4/2})_f(CR_qA_{1-q})_g(CR_rA_{2-r})_h(O(CR_sA_{2-s}))_i(CR_tA_{3-t})_j$, with (C) a catalyst to form a aliphatic unsaturation premix or hydroxy premix respectively; (2") effecting a reaction by adding the aliphatic unsaturation premix or hydroxy premix to (A) at least one organohydrogen cyclosiloxane comprising at least 2 SiH bonds per molecule and having the formula

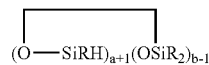

so that ratio of SiH bonds in component (A) to the aliphatic unsaturation or hydroxy group of component (B) is at least 2.5 to form a reaction mixture comprising organohydrogensilicon compounds having at least one SiH bond per molecule described by formula (I)

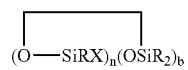  (I)

(3") optionally, adding an inhibitor to the reaction mixture; and (4") optionally, isolating the organohydrogensilicon compounds; where B is boron, each R is independently selected from a hydrogen atom and a monovalent hydrocarbon group comprising 1 to 20 carbon atoms which is free from aliphatic unsaturation, a is an integer from 1 to 18, b is an integer from 1 to 19, a+b is an integer from 3 to 20, each X is an independently selected functional group selected from a halogen atom, an ether group, an alkoxy group, an alkoxyether group, an acyl group, an epoxy group, an amino group, a silyl group, or a $-Z-R^4$ group, where each Z is independently selected from an oxygen and a divalent hydrocarbon group comprising 2 to 20 carbon atoms, each $R^4$ group is independently selected from $-BR_uY_{2-u}$, or a group described by formula (II):

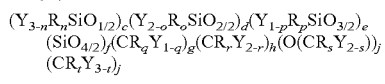  (II)

where B refers to boron, each R is as described above, the sum of $c+d+e+f+g+h+i+j$ is at least 2, n is an integer from 0 to 3, o is an integer from 0 to 2, p is an integer from 0 to 1, q is an integer from 0 to 1, r is an integer from 0 to 2, s is an integer from 0 to 2, t is an integer from 0 to 3, u is an integer from 0 to 2, each A is independently selected from a hydroxy group, a monovalent hydrocarbon group comprising 2 to about 20 carbon atoms having at least one aliphatic unsaturation, a monovalent oxyhydrocarbon group comprising 2 to about 20 carbon atoms having at least one aliphatic unsaturation, or a functional group selected from a halogen atom, an ether group, an alkoxy group, an alkoxyether group, an acyl group, an epoxy group, an amino group, a silyl group, provided at least one A group has an aliphatic unsaturation or a hydroxy group, each Y is an independently selected functional group selected from a halogen atom, an ether group, an alkoxy group, an alkoxyether group, an acyl group, an epoxy group, an amino group, a silyl group, or a Z-G group, where Z is as described above, each G is a cyclosiloxane described by formula (III):

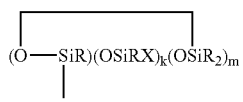

(III)

where R and X are as described above, k is an integer from 0 to 18, m is an integer from 0 to 18, k+m is an integer from 2 to 20, provided in formula (II) that one of the Y groups is replaced by the Z group bonding the $R^4$ group to the cyclosiloxane of formula (I), and provided further (a) at least one X group of Formula (I) is a $-Z-R^4$ group, (b) if Z is a divalent hydrocarbon group, a=1, c=2, e+f+g+h+i+j=0 and d>0, then at least one d unit (i.e. $Y_{2-o}R_oSiO_{2/2}$) contain a -Z-G group or the c units (i.e. $Y_{3-n}R_nSiO_{1/2}$) have no -Z-G group or at least two -Z-G groups, (c) if Z is a divalent hydrocarbon group, a=1, c=2 and d+e+f+g+h+i+j=0, then the c units (i.e. $Y_{3-n}R_n$-$SiO_{1/2}$) have no -Z-G group or at least two -Z-G groups, and (d) if g+h+i+j>0 then c+d+e+f>0.

24. The method of claim 23 further comprising step (2"a) adding at least one hydrocarbon, oxyhydrocarbon or functional compound having at least one aliphatic unsaturation or hydroxy group to the reaction mixture comprising organohydrogensilicon compounds having at least one SiH bond per molecule formed in step 2" so to form a second reaction mixture comprising organohydrogensilicon compounds having at least one SiH bond per molecule where 5 to 70% of the SiH bonds have been converted to a hydrocarbon, oxyhydrocarbon or functional group.

25. The method of claim 24 where the hydrocarbon, oxyhydrocarbon or functional compound having at least one aliphatic unsaturation or hydroxy group is allylglycidylether.

* * * * *